United States Patent [19]

Tanabe

[11] Patent Number: 5,814,509

[45] Date of Patent: Sep. 29, 1998

[54] PROSTACYCLIN SYNTHASE DERIVED FROM HUMAN

[76] Inventor: Tadashi Tanabe, 18-13, Higashitoyonaka-cho 3-chome, Toyonaka-shi, Osaka 569, Japan

[21] Appl. No.: 578,709

[22] PCT Filed: Apr. 27, 1995

[86] PCT No.: PCT/JP95/00838

§ 371 Date: Dec. 28, 1995

§ 102(e) Date: Dec. 28, 1995

[87] PCT Pub. No.: WO95/30013

PCT Pub. Date: Nov. 9, 1995

[30] Foreign Application Priority Data

Apr. 28, 1994 [JP] Japan ................................... 6-114316

[51] Int. Cl.$^6$ .............................. A01N 43/04; C12N 9/90; C12N 5/00; C07H 21/04

[52] U.S. Cl. ...................... 435/233; 435/320.1; 435/325; 435/252.3; 514/44; 536/23.2; 935/22

[58] Field of Search ............................... 435/183, 240.1, 435/252.3, 320.1, 233, 325; 514/44; 536/23.2; 935/22

[56] References Cited

PUBLICATIONS

Bimodal Distribution of the Prostaglandin $I_2$ Synthase Antigen in Smooth Muscle Cells, W. Smith et al, *The Journal of Biological Chemistry*, pp. 5922–5926, dtd. 1983.

Purification, Quantitation, and Localization of $PGI_2$ Synthase Using Monoclonal Antibodies, W. Smith et al, pp. 87–92, dtd. 1983.

Eighth Gaddum Memorial Lecture University of London Institute of Education Dec. 1980, Biological Importance of Prostacyclin, S. Moncada, pp. 1–31, dtd 1982.

Agonist–Specific Desensitization of $PGI_2$–Stimulated Cyclic AMP Accumulation by $PGE_1$ In Human Foreskin Fibroblasts, R. Gorman et al, pp. 3–17, dtd. 1980.

Cytochrome P–450, Biochemistry, Biophysics and Environmental Implications, Proceedings of the 4th International Conference on Cytochrome P–450 held in Kuopio, Finland, May 31–Jun. 3, 1982, E. Hietanen et al, eds., pp. 103–106, dtd. 1982.

Purification of Prostacyclin Synthase from Bovine Aorta By Immunoaffinity Chromatography, D. DeWitt et al, *The Journal of Biological Chemistry*, pp. 3285–3293, dtd. Mar. 1983.

Molecular Characterization of the Prostacyclin Synthase, *Advances in Prostaglandin, Thromboxane, and Leukotriene Research*, M. Inoue, pp. 29–33, dtd. 1987.

Bovine Prostacyclin Synthase: Purification and Isolation of Partial cDNA, *Biochemical and Biophysical Research Communications*, B. Pereira et al, pp. 1041–1048, dtd. 1993.

Structure–function relationships of membrane–bound heme–enzyme, cytochrome P450, Institute for Chemical Reaction Science, Tohoku University, T. Shimizu, pp. 10–15, dtd. 1992.

Preparation and Assay of Prostacyclin Synthase, Methods in Enzymology, J. Salmon et al, pp. 91–99, dtd. 1982.

Molecular Cloning of Prostacyclin Synthase From Bovine Endothelial Cells, *Eicosandoids & Other BioActive Lipids in Cancer, Inflammation & Radiation Injury*, T. Tanabe et al, p. 137, dtd. 1993.

Molecular Cloning and Expression of Human Prostacyclin Synthase, *Biochemical and Biophysical Research Communications*, A. Miyata et al, pp. 1728–1734, dtd. 1994.

Isolation and Molecular Cloning of Prostacyclin Synthase from Bovine Endothelial Cells, *The Journal of Biological Chemistry*, S. Hara et al, pp. 19897–19903, dtd. 1994.

Molecular Cloning and Chracterization of Bovine Prostacyclin Synthase, *Biochemical and Biophysical Research Communications*, B. Pereira et al, pp. 59–65, dtd. 1994.

Ngo et al. (1994) Computational Complexity, Protein Structure Prediction, and the Levinthal Paradox. In: The Protein Folding Proble and Tertiary Structure Prediction, Eds. Merz et al., Birkhauser, Boston, MA, pp. 491–495, Jan. 1994.

*Primary Examiner*—Robert A. Wax
*Assistant Examiner*—Einar Stole
*Attorney, Agent, or Firm*—Sughrue, Mion, Zinn, Macpeak & Seas, PLLC

[57] ABSTRACT

The present invention clarifies the primary structure of human-originated PGIS and the nucleotide sequence encoding same. The PGIS and its DNA are useful as reagents for the development of therapeutic agents for the cardiovascular diseases induced by the production imbalance between $PGI_2$ and $TXA_2$, and as diagnostics for determining the in vivo tissue expression level and distribution of PGIS or mRNA thereof. Moreover, they can be used as therapeutic agents for cardiovascular diseases, which introduce PGIS and the like into human or other animals in a lesion-specific manner. The production method of the present invention is useful for the easy and efficient mass production of the human-originated PGIS. The antibody of the present invention is useful for the purification of the human-originated PGIS and immunohistochemical analysis of the cause of a disease.

19 Claims, 13 Drawing Sheets

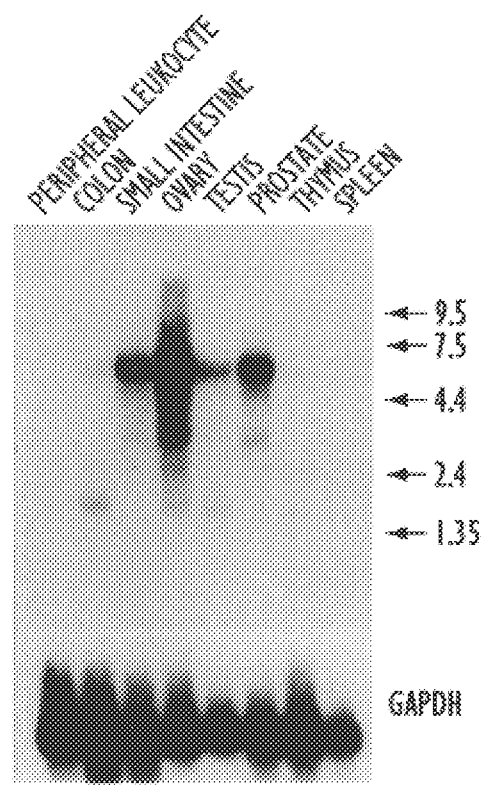

PROSTACYCLIN SYNTHASE DERIVED FROM HUMAN

TECHNICAL FIELD

The present invention relates to a polypeptide having an amino acid sequence of human-originated prostacyclin synthase (hereinafter referred to as PGIS), a DNA encoding same, a vector containing said DNA, a host cell transformed with said vector and a method for preparing human-originated PGIS comprising culturing said host cell. The present invention also relates to an antibody having a reactivity with said PGIS or its fragment. Moreover, the present invention relates to a pharmaceutical composition comprising said DNA or a vector containing said DNA, a method for promoting the production of prostaglandin $I_2$ and a method for the treatment of the diseases induced by a low production of prostaglandin $I_2$.

BACKGROUND ART

PGIS is mainly contained in microsomal fractions of vascular endothelial cells, and is an enzyme that catalyzes synthesis of prostaglandin $I_2$ (hereinafter referred to as $PGI_2$), that is, conversion of prostaglandin $H_2$ (hereinafter referred to as $PGH_2$) to $PGI_2$.

$PGI_2$ synthesized by this enzyme has potent platelet aggregation-inhibitory action and vascular smooth muscle-relaxing action. On the other hand, platelets contain thromboxane $A_2$ (hereinafter referred to as $TXA_2$) having strong platelet aggregation action and vascular smooth muscle-contracting action, and the both substances act antagonistically in the vascular system to maintain homeostasis [British Journal of Pharmacology, vol. 76, p 3 (1982)].

Cardiovascular diseases such as myocardial infarction, thrombosis and arteriosclerosis, which are among the adult diseases, have recently been considered to be caused by the imbalance in the vascular production of $PGI_2$ and TXA2, particularly, insufficient vascular function due to low production of $PGI_2$ (ibid.).

For the therapeutic treatment of the diseases presumably induced by the low production of $PGI_2$, $PGI_2$ may be supplemented as a pharmaceutical product from the outside of the body. However, $PGI_2$ is chemically extremely unstable to the extent that a practical use of $PGI_2$ itself as a pharmaceutical product may be unrealizable. In view of such situation, for example, stable $PGI_2$ analogs such as blood coagulation inhibitor or vasodilator are under development.

The homeostasis in human and other animals which is inherently based on the balance between $PGI_2$ and TXA2 may possibly destroyed by the administration of stable $PGI_2$ analogs. That is, administration of stable $PGI_2$ analogs in large amounts is associated with a risk of lowering the responsiveness of cells to $PGI_2$, thus impairing its capability of responding to $PGI_2$ when such responsiveness is in urgent need [Prostaglandins, vol. 19, p 2 (1980)].

For correcting the imbalance between $PGI_2$ and $TXA_2$ and attempting the recovery of normal functions of the vascular system in an expectation of therapeutic effect over thrombosis and the like, chemically stable analogs may be used. Alongside therewith, moreover, elucidation of physicochemical property and biological property of PGIS, clarification of the relations between PGIS production and $PGI_2$ production while using said PGIS or DNA encoding PGIS as a research sample, and development of said PGIS or DNA encoding PGIS as pharmaceutical products to regulate the production of $PGI_2$ are considered to be important and significant for the treatment of the above-said various diseases caused by the imbalance between $PGI_2$ and $TXA_2$.

Conventionally, there has been reported the tissue distribution of PGIS, namely, its presence in vascular endothelial cells, non-vascular smooth muscle cells and arterial smooth muscle of various organs [Advances in Prostaglandin, Thromboxane, and Leukotriene Research, vol. 11, pp. 87–92 (1983) and J. Biol. Chem., vol. 258, No. 9, pp. 5922–5926 (1983)]. Meanwhile, isolation and purification of PGIS from porcine and bovine have been tried [porcine: Cytochrome P450, Biochemistry, Biophysics and Environmental Implications, pp. 103–106 (1982); bovine: J. Biol. Chem., vol. 258, No. 9, pp. 3285–3293 (1983)] and N-terminal amino acid sequence and partial downstream amino acid sequence of bovine PGIS have been reported [Advances in Prostaglandin, Thromboxane, and Leukotriene Research, vol. 17, pp. 29–33 (1987) and Biochemical and Biophysical Research Communications, vol. 197, No. 3, pp. 1041–1048 (1993)].

However, isolation, purification and amino acid sequence of human PGIS have not been elucidated.

DISCLOSURE OF THE INVENTION

An object of the present invention is to clarify an amino acid sequence of PGIS derived from human and provide said human-originated PGIS and DNA encoding said PGIS.

Said PGIS and DNA encoding said PGIS are useful as reagents for ① the analysis of the physicochemical and biological properties of PGIS at the molecular or genetic level; ② the analysis of the mechanism controlling the production of PGIS and the mechanism controlling the production of $PGI_2$ by PGIS; and ③ the investigation of the cause of various cardiovascular diseases considered to be induced by the production imbalance between $PGI_2$ and $TXA_2$, and the molecular or genetic level analysis for the development of therapeutic agents for said diseases. In addition, PGIS and its mRNA are useful as diagnostics for the determination of expression level and distribution in the body tissues. Still further, they are expected to provide therapeutic agents for, for example, various cardiovascular disorders such as thrombosis, myocardial infarction, arteriosclerosis and angina pectoris, which enhance the production level of $PGI_2$ upon introduction of themselves, fragment thereof or modified compound thereof into the body in a lesion-specific manner.

Another object of the present invention is to provide a recombinant vector containing a DNA encoding human-originated PGIS, the expression system of PGIS which comprises a host cell transformed with said vector, and a method for preparing PGIS by genetic engineering using said expression system.

According to such method, human-originated PGIS can be prepared in great amounts with ease and with high efficiency.

The present invention also aims at providing a human-originated PGIS antibody useful for the purification of human-originated PGIS and immunohistochemical analysis of the cause of a disease.

The present inventor has conducted intensive studies with the aim of accomplishing the above-mentioned objects, and succeeded in cloning cDNA encoding PGIS from human aorta endothelial cells and identifying the primary structure of human-originated PGIS from the nucleotide sequence of said cDNA, which resulted in the completion of the present invention.

Accordingly, the present invention relates to a DNA comprising a DNA having a nucleotide sequence encoding an amino acid sequence of human-originated PGIS substantially depicted in Sequence No. 15, preferably a DNA comprising a DNA having a 28th–1527th nucleotide sequence substantially shown in Sequence No. 14, and more preferably a DNA having a 28th–1527th nucleotide sequence shown in Sequence No. 14.

The present invention also relates to a recombinant vector comprising the above-mentioned DNA, a host cell transformed with said vector and a method for preparing human-originated PGIS comprising culturing said host cell in a medium and recovering human-originated PGIS from the obtained culture.

The present invention also relates to a polypeptide having an amino acid sequence of human-originated PGIS which is substantially shown in Sequence No. 15, and antibodies having reactivities with said human-originated PGIS.

The present invention further relates to a pharmaceutical composition comprising said DNA or a recombinant vector comprising said DNA. Said pharmaceutical composition can be used as a medicament for promoting $PGI_2$ production or for treating the diseases induced by a low production of $PGI_2$.

The present invention moreover relates to a method for promoting the production of $PGI_2$, comprising introducing the above-mentioned DNA or a recombinant vector comprising said DNA into human or other animals. The present invention also relates to a method for treating the diseases induced by a low production of $PGI_2$, comprising introducing the above-mentioned DNA or a recombinant vector comprising said DNA into human or other animals.

BRIEF DESCRIPTION OF THE DRAWINGS

FIG. 13 is a photograph showing the distribution of PGIS mRNA expression in human body (peripheral leukocyte, large intestine, small intestine, ovary, testicle, prostate, thymus and spleen) by electrophoresis.

DETAILED DESCRIPTION OF THE INVENTION

Figure 1:
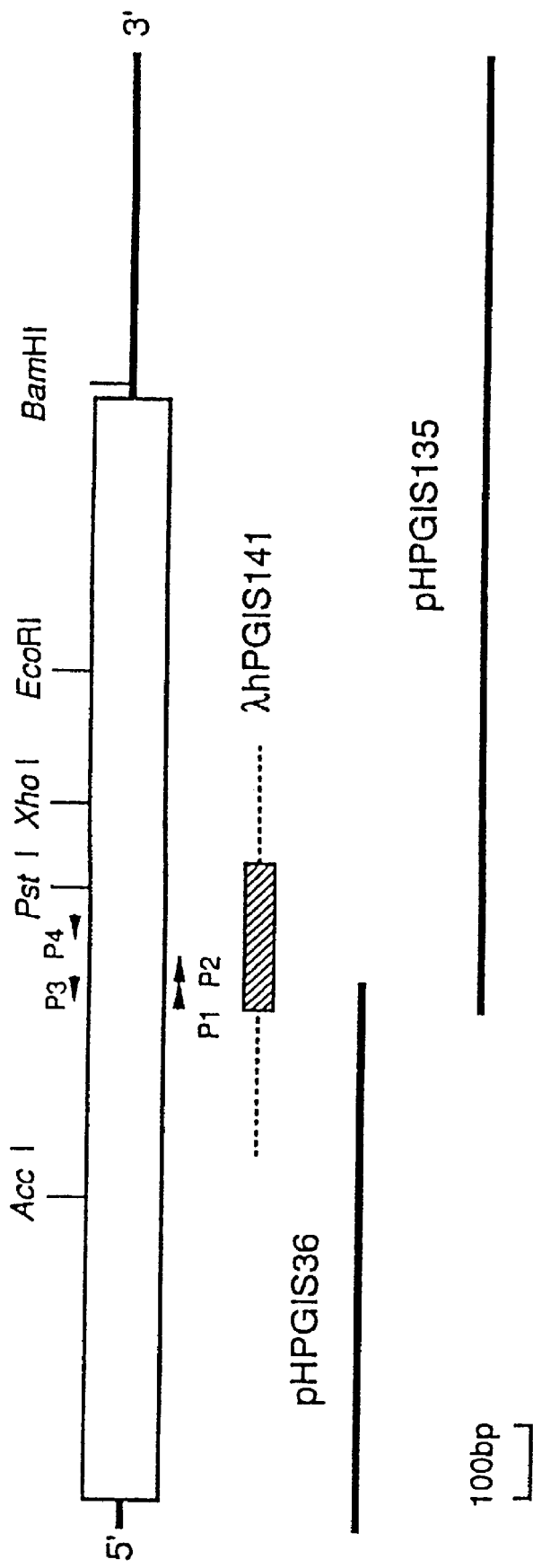
FIG. 1 shows a restriction enzyme map of human PGIS cDNA, and the PGIS DNA region comprised in λ hPGIS141, pHPGIS135 and pHPGIS36.

The present invention is explained in detail in the following.

The polypeptide of the present invention has a catalytic activity to convert $PGH_2$ to $PGI_2$ and has an amino acid sequence of human-originated PGIS substantially shown in Sequence Listing, Sequence No. 15 to be mentioned later.

By "substantially" is meant that the polypeptide of the present invention is not limited to the polypeptide having the amino acid sequence shown in Sequence No. 15, but may include deletion, substitution and addition with respect to some of the amino acids in the amino acid sequence shown in Sequence No. 15, as long as the polypeptide has immunological and biological activity (human PGIS activity) similar to that of human-originated PGIS having said amino acid sequence.

While the site of deletion, substitution and addition of the amino acids is not particularly limited, at least 441st Cys residue and thereabout region in the amino acid sequence shown in Sequence No. 15 need to be reserved. This is because human-originated PGIS of the present invention is homologous to known cytochrome P450 in the amino acid sequence, since it has Cys residue in the C-terminal side of the amino acid sequence constituting the heme-binding site (fifth ligand) which is important for the expression of biological activity of cytochrome P450, and speculated to be a new protein belonging to the cytochrome P450 family [see *Seibutsu Butsuri*, vol. 32, No. 1, pp. 10–15 (1992)].

The polypeptide of the present invention preferably has an amino acid sequence of human-originated PGIS shown in Sequence No. 15.

The PGIS activity possessed by the polypeptide of the present invention is a catalytic activity to convert $PGH_2$ to $PGI_2$. Said PGIS activity can be determined according to the method of Salmon, J. A. and Flower, R. J. et al [Methods Enzymol., 86, pp. 91–99 (1982)] wherein the conversion of $^{14}C$-labeled $PGH_2$ to $PGI_2$ is assayed by separating the metabolite of 6-keto-$PGF_1\alpha$ by thin layer chromatography and detecting the radioactivity of said 6-keto-$PGF_1\alpha$.

The present invention also relates to a DNA comprising a DNA having a nucleotide sequence encoding the amino acid sequence of human-originated PGIS substantially shown in Sequence No. 15.

Said DNA may be any as long as it comprises a DNA having a nucleotide sequence encoding the aforementioned amino acid sequence of human-originated PGIS, and is exemplified by a DNA encoding the polypeptide having the amino acid sequence shown in Sequence No. 15 or a polypeptide having the equivalent immunological and biological activity. More specifically, it is a DNA comprising the 28th–1572th nucleotide sequence in the nucleotide sequence shown in Sequence No. 14.

In general terms, the genetic recombinant technique enables conversion of at least one nucleotide of a DNA sequence of a gene to a different nucleotide according to the degeneracy of the genetic code, without changing the amino acid sequence of a protein produced by the gene. Accordingly, the DNA of the present invention encompasses a DNA comprising a nucleotide sequence obtained by modification for substitution, based on the genetic code, of the 28th–1527th nucleotide sequence of Sequence Listing Sequence No. 14.

The DNA of the present invention can be obtained by any method. For example, the present invention encompasses complementary DNA (cDNA) prepared from mRNA, DNA prepared from genomic DNA, DNA obtained by chemical synthesis, DNA obtained by amplification by PCR using RNA or DNA as a template, and DNA constructed by suitably combining these methods.

The DNA of the present invention can be obtained by a method comprising cloning cDNA from mRNA of human-originated PGIS by a conventional method, a method comprising splicing an isolated genomic DNA for PGIS, a method comprising chemical synthesis or other method.

(1) For example, a method for cloning cDNA from mRNA encoding human-originated PGIS comprises the following steps.

Cells producing human-originated PGIS, such as human aorta endothelial cells are cultured and mRNA encoding said PGIS is prepared from the culture thereof. mRNA is prepared by, for example, applying entire RNA prepared by a known method such as guanidine thiocyanate method [Chirgwin, J. M. et al., Biochem., 18, 5294 (1979)], heat phenol method and AGPC to affinity chromatography using oligo(dT)-cellulose or poly U-sepharose.

Using the obtained mRNA as a template, cDNA chain is synthesized by a known method using a reverse transcriptase [e.g., the method of Okayama, H. et al: Okayama, H. et al., Mol. Cell. Biol., 2, 161 (1982) and ibid. 3, 280 (1983)], and the method of Gubler, U. and Hoffman, B. J.: Gubler, H. and Hoffman, B. J., Gene, 25, 263 (1983)], thereby converting the same to a double stranded cDNA. This cDNA is inserted into a plasmid vector or a phage vector, with which *Escherichia coli* is transformed, or transfected after in vitro packaging, to prepare cDNA library.

The plasmid vector used here is not subject to any particular limitation as long as it can be retained by replication in the host, and the phage vector is not limited either as long as it can proliferate in the host. Examples of the conventionally-used cloning vector include pUC119, λ gt10 and λ gt11. When immunological screening to be mentioned later is to be employed, the vector preferably contains a promoter capable of expressing the PGIS gene in the host.

The method for insertion of a cDNA into plasmid is exemplified by a method described in Maniatis, T. et al [Molecular Cloning, A Laboratory Manual, Cold Spring Harbor Laboratory, p. 239 (1982)]. The method for insertion of a cDNA into phage vector includes the method of Hyunh, T. V. et al [DNA Cloning, a practical approach, 1, 49 (1985)]. For simplification, a commercially available ligation kit (e.g., those manufactured by Takara Shuzo) can be used. The recombinant plasmid and phage vector thus obtained are introduced into a suitable host such as prokaryotic cells (e.g., *E. coli* HB101, DH5 and MC1061/P3).

The method for introducing a plasmid into a host includes calcium chloride method and calcium chloride/rubidium chloride method described in Maniatis, T. et al [Molecular Cloning, A Laboratory Manual, Cold Spring Harbor Laboratory, p. 239 (1982)] and electroporation method. The method for introducing a phage vector into a host is exemplified by a method comprising in vitro packaging of phage DNA and introducing same into proliferated host cells. In vitro packaging can be carried out easily by using a commercially available in vitro packaging kit (e.g., product of Stratagene and product of Amersham).

The cDNA encoding the PGIS of the present invention can be isolated from the cDNA library prepared by the above method, by a combination of general cDNA screening methods.

Such methods include, for example, a method wherein an oligonucleotide considered to be corresponding to the amino acid sequence of human PGIS is chemically synthesized separately and labeled with $^{32}P$ to give a probe, and a clone having the desired cDNA is screened by a known colony hybridization [Crunstein, M. and Hogness, D. S., Proc. Natl. Acid. Sci. USA, 72, 3961 (1975)] or plaque hybridization [Molecular Cloning, A Laboratory Manual, Cold Spring Harbor Laboratory, p. 239 (1982)]; and a method wherein PCR primer is prepared and a specific region of PGIS is amplified by PCR method, which is followed by selecting a clone having a DNA fragment encoding said region. When a cDNA library prepared using a vector (e.g. λ gt11 phage vector) capable of expressing cDNA is used, the objective clone can be selected based on an antigen-antibody reaction using the PGIS antibody of the present invention to be mentioned later. When large amounts of clone are treated, screening based on PCR is preferable.

The nucleotide sequence of DNA thus obtained can be determined by Maxam-Gilbert method [Maxam, A. M. and Gilbert, W., Proc. Natl. Acad. Sci. USA., 74, 560 (1977)] or synthetic dideoxynucleotide chain termination method using phage M13 [Sanger, F. et al, Proc. Natl. Acad. Sci. USA., 74, 5463–5467 (1977)]. The PGIS gene can be obtained by cleaving all or part thereof from the clone obtained above by using a restriction enzyme and the like.

(2) A preparation method comprising isolating DNA encoding PGIS from genomic DNA of human aorta vascular cells includes, for example, the following method.

Human aorta vascular cells are lysed preferably using SDS or protenase K, and DNA is deproteinized by repetitive extraction with phenol. RNA is preferably digested with ribonuclease. The obtained DNA is partially digested with a suitable restriction enzyme and the obtained DNA fragment is amplified by a suitable phage or cosmid to form a library. Then, the clone having the desired sequence is detected by, for example, a method using a DNA probe with a radioactive label, and a whole or partial PGIS gene is cleaved from said clone by using a restriction enzyme and the like.

(3) The DNA of the present invention can be prepared by chemical synthesis by a conventional method based on the nucleotide sequence depicted in Sequence Listing Sequence No. 14.

The present invention further relates to a recombinant vector comprising DNA encoding the above-mentioned PGIS. The recombinant vector of the present invention is not particularly limited as long as it can be retained by replication or self-proliferation in various prokaryotic and/or eukaryotic host cells, and includes plasmid vector and phage vector.

The recombinant vector can be easily prepared by ligating the DNA encoding human-originated PGIS of the present invention with a commercially available recombinant vector (plasmid DNA and bacteriophage DNA) by a conventional method. Usable recombinant vector includes, for example, *Escherichia coli*-originated plasmids pBR322, pBR325, pUC12 and pUC13; yeast-originated plasmids pSH19 and pSH15; and *Bacillus subtilis*-originated plasmids pUB110, pTP5 and pC194. Examples of phage include bacteriophage such as λ phage, and animal or insect viruses such as retrovirus, vaccinia virus, nuclear polyhedrosis virus and adenovirus [e.g. pVL1392, pBK283, *Autographa californica* nuclear polyhedrosis virus (AcNPV) and *Bombyx mori* nuclear polyhedrosis virus (BmNPV)].

When production of PGIS by the expression of the PGIS gene is aimed, an expression vector is useful. The expression vector is not particularly limited as long as it expresses the PGIS gene in various prokaryotic and/or eukaryotic host cells and is capable of producing proteins. Preferred are that derived from insect virus which infects insect cells and produces PGIS in said cells, and that derived from animal virus which infects animal cells and produces PGIS in said cells.

When bacteria, particularly *Escherichia coli*, is used as the host cell, the expression vector generally consists of at least promoter-operator region, initiation codon, DNA encoding the PGIS of the present invention, termination codon, terminator region and replicon.

When yeast, animal cell or insect cell is used as the host cell, the expression vector preferably consists of at least promoter, initiation codon, DNA encoding the polypeptide of the present invention and termination codon. It may contain DNA encoding signal peptide, enhancer sequence, non-translation region on the 5' or 31' side of the polypeptide of the present invention, splicing junction, polyadenylation site, selection marker region, replicon and the like.

The promoter-operator region for expressing the polypeptide of the present invention in bacteria contains promoter, operator and Shine-Dalgarno (SD) sequence such as AAGG. When the host is *Escherichia coli*, the region preferably contains, for example, Trp promoter, lac promoter, recA promoter, λ PL promoter and lpp promoter. The promoter for expressing PGIS in yeast includes, for example, PH05 promoter, PGK promoter, GAP promoter and ADH promoter, and when the host is bacteria belonging to the genus Bacillus, SL01 promoter, SP02 promoter and penP promoter can be used. When the host is eukaryotic cells such as animal cells, examples of the promoter include, but not limited to, SV40-derived promoter, retrovirus promoter, heat shock promoter, polyhedron promoter that a nuclear polyhedrosis virus has, cytomegalovirus promoter, adenovirus promoter and β-actin promoter. The use of an enhancer is also effective for the expression.

Preferable initiation codon includes, for example, methionine codon (ATG).

The termination codon is exemplified by conventional termination codons such as TAG and TGA.

As the terminator region, conventional intact or synthetic terminator can be used.

By replicon is meant a DNA capable of reproducing the entire DNA sequence in the host cell, and exemplified by naturally occurring plasmid, artificially modified plasmid (DNA fragment prepared from naturally occurring plasmid) and synthetic plasmid. Examples of preferable plasmid include plasmid pBR322 and artificial modification thereof (DNA fragment obtained by treating pBR322 with a suitable restriction enzyme) in the case of *E. coli*; yeast 2µ plasmid and yeast chromosomal DNA in the case of yeast; and plasmid pRSVneo ATCC 37198, plasmid pSV2dhfr ATCC 37145, plasmid pdBPV-MMTneo ATCC 37224 and plasmid pSV2neo ATCC 37149 in the case of mammalian cell.

Enhancer sequence, polyadenylation site and splicing junction site can be those conventionally used by artisan, such as respective ones derived from SV40.

As the selection marker, conventional ones can be used according to a conventional method. Examples thereof include a gene resistant to antibiotic such as tetracycline, ampicillin and kanamycin.

The expression vector of the present invention can be prepared by ligating at least the above-mentioned promoter, initiation codon, DNA encoding PGIS of the present invention, termination codon and terminator region sequentially and cyclically into a suitable replicatable unit. For this end, suitable DNA fragments such as linker and other restriction sites can be used by a conventional method such as digestion with restriction enzyme and ligation using T4DNA ligase on demand.

The transformant of the present invention can be prepared by introducing the above-mentioned expression vector into a host cell.

Examples of the host cell include microorganisms such as bacteria (e.g. bacteria belonging to the genera Escherichia and Bacillus), yeast such as those belonging to the genus Saccharomyces, animal cells and insect cells. Specifically exemplified are *Escherichia coli* K12DH1, M103, JA221, HB101, C600, XL-1 Blue and JM109 as the bacteria belonging to the genus Escherichia; and *Bacillus subtilis* 207-21 as the bacteria belonging to the genus Bacillus. Examples of the yeast include *Saccharomyces cerevisiae* AH22, AH22R-, NA87-11A and DKD-5D. Examples of animal cell include simian cell COS-7, Vero, Chinese hamster cell CHO, mouse L cell, human FL cell and human 293 cell. Examples of insect cell include BmN4 and Sf9. Preferred are insect cells and animal cells.

The preferred host cell for cloning the DNA sequence and constructing the vector is generally a prokaryotic cell. The expression vector constructed is used to transform a suitable host cell. The host cell may be a prokaryotic cell or an eukaryotic cell as well. Preferred are insect cells (e.g., BmN4 and Sf) and animal cells.

The expression vector is introduced (i.e., transformation which is used in a concept inclusive of transfection in the present invention) into host cells by a conventionally known method.

For example, in the case of bacteria (e.g. *Escherichia coli* and *Bacillus subtilis*), the method of Cohen et al [Proc. Natl. Acad. Sci. USA., 69, 2110 (1972)], protoplast method [Mol. Gen. Genet., 168, 111 (1979)] or competent method [J. Mol. Biol., 56, 209 (1971)] may be used; in the case of *Saccharomyces cerevisiae*, the method of Hinnen et al [Proc. Natl. Acad. Sci. USA., 75, 1927 (1978)] or lithium method [J. Bacteriol., 153, 163 (1983)] may be used; in the case of animal cells, the method of Graham [Virology., 52, 456 (1973)], lipofectin method or HVJ-liposome method [Hypertension, 21, 894–899 (1993)] may be used; and in the case of insect cells, the method of Summers et al [Mol. Cell. Biol., 3, 2156–2165 (1983)] may be used for transformation.

The human-originated PGIS of the present invention can be prepared by culturing, in a nutrient medium, a transformant (which term is used in a concept inclusive of transfectant in the present invention) comprising the expression vector prepared as in the above.

The nutrient medium preferably contains carbon source, inorganic nitrogen source or organic nitrogen source necessary for the growth of host cell (transformant). Examples of carbon source include glucose, dextran, soluble starch and sucrose; examples of inorganic nitrogen source or organic nitrogen source include ammonium salts, nitric acid salts, amino acid, corn steep liquor, peptone, casein, meat extract, soybean meal and potato liquid extract. When desired, other nutrients such as inorganic salt (e.g. calcium chloride, sodium dihydrogenphosphate and magnesium chloride), vitamins, and antibiotics such as ampicillin and kanamycin may be added to the medium.

Culture is carried out according to the method known in the pertinent field. Culture conditions such as temperature, pH of the medium and culture time are appropriately determined so that the maximum potency of PGIS can be obtained.

Specific media and culture conditions to be employed according to the host cell are exemplified in the following, which are not limitative.

When the host is bacteria, Actinomyces, yeast or filamentous fungus, for example, liquid media containing the above-mentioned nutrient sources are appropriate. Preferred is a medium having a pH of 5–8.

When the host is *Escherichia coli*, preferable medium is M9 medium [Miller, J., Exp. Mol. Genet., p. 431, Cold Spring Harbor Laboratory, New York (1972)]. In this case, culture is performed with aeration and agitation as necessary, at 14°–43° C. for about 3 to 24 hours.

When the host is bacteria belonging to the genus Bacillus, culture is performed with aeration and agitation as necessary, at 30°–40° C. for about 16 to 96 hours.

When the host is yeast, the medium is exemplified by Burkholder minimum medium [Bostian, K. L. et al, Proc. Natl. Acad. Sci. USA, 77, 4505 (1980)] which preferably has a pH of 5–8. Culture is generally performed at about 20°–35° C. for about 14 to 144 hours with aeration and agitation where necessary.

When the host is animal cell, the medium is exemplified by MEM medium containing fetal calf serum at about 5–20% [Science, 122, 501 (1952)], DMEM medium [Virology, 8, 396 (1959)], RPMI1640 medium [J. Am. Med. Assoc., 199, 519 (1967)] and 199 medium [Proc. Soc. Exp. Biol. Med., 73, 1 (1950)]. The pH of the medium is preferably about 6–8, and culture is generally performed at about 30°–40° C. for about 15–60 hours with aeration and agitation where necessary.

When the host is insect cell, the medium is exemplified by Grace's medium containing fetal calf serum [Proc. Natl. Acad. Sci. USA, 82, 8404 (1985)] which preferably has a pH of about 5–8. Culture is generally performed at about 20°–40° C. for about 15 to 100 hours with aeration and agitation where necessary.

The human-originated PGIS of the present invention can be recovered as in the following from the culture obtained above.

That is, when the human-originated PGIS is present in the liquid portion of the culture, the culture thus obtained is subjected to filtration or centrifugation to separate culture filtrate (supernatant), and PGIS is purified and separated from said culture filtrate by a conventional method employed for purifying and isolating natural or synthetic proteins.

The method for purification and isolation includes, for example, a method utilizing the solubility, such as salting out and solvent precipitation, a method utilizing the difference in molecular weights such as dialysis, ultrafiltration, gel filtration and sodium dodecyl sulfate-polyacrylamide gel electrophoresis, a method utilizing charge such as ion exchange chromatography and hydroxyapatite chromatography, a method utilizing specific affinity such as affinity chromatography, a method utilizing the difference in hydrophobicity such as reversed phase high performance liquid chromatography and a method utilizing difference in isoelectric point such as isoelectric focusing.

When the human-originated PGIS is present in the periplasm or cytoplasm of the cultured transformant, the culture is subjected to a conventional method such as filtration and centrifugation to collect the cells; the cells are suspended in a suitable buffer and subjected to lysis of cell wall and/or cell membrane by ultrasonication, using lysozyme or by freeze-thawing; and the membrane fraction containing PGIS is obtained by centrifugation or filtration. Said membrane fraction is solubilized with surfactant such as Triton to give a crude solution. The crude solution is treated by a conventional method as exemplified supra to isolate and purify PGIS of the present invention.

The present invention also relates to an antibody having a reactivity with the above-said human-originated PGIS. The antibody of the present invention encompasses both the polyclonal antibody and monoclonal antibody having the above-mentioned properties. The antibody of the present invention can be obtained by a conventional method.

For example, the monoclonal antibody of the present invention can be prepared from hybridoma produced by so-called cell fusion. That is, fused hybridoma is formed from the antibody-producing cell and bone marrow cell; said hybridoma is cloned; and a clone is selected which produces an antibody having a specific affinity for an antigen, i.e. a polypeptide having part or whole of the human-originated PGIS amino acid sequence. The procedure therefor may be known methods except the use of the human-originated PGIS of the present invention as an immunizing antigen.

The immunogen can be used for immunizing animals after admixing with, for example, complete Freund adjuvant. Examples of the animal include mouse, rat and rabbit. The animals are immunized by subcutaneous, intramuscular or intraperitoneal injection of about 5–200 μg/injection. The immunization includes 1–4 times of immunization at about every 1–2 weeks from the initial immunization and final immunization at about 1–4 weeks thereafter. When about 3–5 days have passed since final immunization, antibody-producing cells are separated from the immunized animal. The antibody-producing cells are exemplified by spleen cells and lymph node cells.

The bone marrow cells are, for example, those derived from mouse, rat and human. Examples thereof include mouse myeloma P3.X63.Ag8, P3.X63.Ag8-U1, P3.NS1-Ag4, SP2/0-Ag14 and X63-Ag8 . 653. It is preferable that the antibody-producing cells and bone marrow cells be derived from the same species of animals.

Cell fusion is performed by the method described in, for example, Nature, vol. 266, p. 550 (1977) or an analogous method. Specifically, it is performed using 30–50% polyethylene glycol having an average molecular weight of 1,000–4,000 at 30°–40° C. for about 1–3 minutes.

The cells obtained by cell fusion are subjected to screening for a clone which produces the desired monoclonal antibody. That is, the cells are cultured in, for example, a microplate and the antibody titer of the culture supernatant in the well in which cell growth was acknowledged is determined by, for example, enzyme antibody method to obtain the well in which suitable antibody has been produced. Cloning by, for example, limiting dilution from such well gives clones. The monoclonal antibody of the present invention can be obtained by culturing said hybridoma cell clone by conventional culture method, high density culture method or spinner-flask culture method and purification thereof by affinity chromatography using protein A-bound carrier or anti-mouse immunoglobulin-bound carrier.

Alternatively, the cultured hybridoma cells are intraperitoneally injected to the mouse of the same species which has been previously treated with pristance, and ascites obtained is subjected to salting out with ammonium sulfate and DEAE ion exchange chromatography to give purified IgG fraction containing the same.

The DNA encoding the human-originated PGIS of the present invention can be used for gene therapy.

The DNA encoding the human-originated PGIS of the present invention or a recombinant vector comprising said DNA is introduced into human or other animals, whereby PGIS is produced in the human or other animals to promote production of $PGI_2$. The promoted $PGI_2$ production in turn enables treatment (therapeutic treatment or improvement of symptoms) of the diseases induced by a low production of $PGI_2$. Examples of the diseases induced by the low production of $PGI_2$ include cardiovascular diseases such as thrombosis, myocardial infarction, arteriosclerosis and angina pectoris. The recombinant vector may be introduced into human or other animals in the form of cells transformed with said recombinant vector.

The gene therapy utilizing the gene (inclusive of DNA and recombinant vector) of the present invention permits setting an appropriate environment in which the gene of the present invention introduced into a human or other animal can fully show its function. The treatment can be given by a conventional method as long as it intends expression of desired effects of the gene of the present invention. Such method is exemplified by virological means utilizing retrovirus vector or adenovirus vector, physical means for introducing gene by particle gun method or by using naked DNA, and chemical means such as lipid method [Molecular Medicine, vol. 30, No. 12, p. 1526 (1993); Jikken Igaku, vol. 12, No. 3, p. 15, 28 and 40 (1994); Proc. Natl. Acad. Sci. USA, 92, 1137 (1995)]. A method using an adenovirus vector which can be used for the gene therapy of cystic fibrosis and which is known to permit efficient introduction of gene into differentiated cells and tissues and expression therein, and a method using a fusogenic liposome which allows introduction of optional gene into tissue cells in vivo are preferable for the gene treatment of the present invention.

The dose of the DNA or recombinant vector of the present invention is subject to appropriate change according to sex, age and body weight of patients, the kind of disease and symptoms thereof, and administration route. For example, 100 µg–10 mg of DNA is generally administered.

The DNA and recombinant vector of the present invention are administered by intravenous injection, transmucosal administration, oral administration using enteric-coated agents, or topical administration, with preference given to topical administration using catheter and the like.

The DNA encoding human-originated PGIS and recombinant vector comprising said DNA of the present invention are admixed with conventional, pharmaceutically acceptable carrier, excipient, diluent, extender, disintegrator, stabilizer, preservative, buffer, emulsifier, flavor, coloring, sweetener, thickener, elixir, solubilizer and other additives such as water, salt solution, phosphate buffer, vegetable oil, ethanol, polyethylene glycol, glycerol, gelatin, lactose, glucose, mannitol, starch, sucrose, magnesium stearate, hydroxypropylcellulose, talc, lanolin and petrolatum, and can be use used in the form of injection, tablet, powder, capsule, enteric-coated agent, ointment, suspension, emulsion, spray, inhalant, collunarium and the like.

A pharmaceutical composition comprising the DNA or recombinant vector comprising said DNA of the present invention can be administered to mammals such as human, mouse, rat, rabbit, pig, cow, sheep, dog and cat.

EFFECTS OF THE INVENTION

The present invention gives the first clarification of the amino acid sequence of human-originated PGIS and nucleotide sequence of DNA encoding the enzyme having said sequence. Based on the elucidation of such amino acid sequence and nucleotide sequence, the present invention provides a method for preparing PGIS by genetic engineering and an expression system related thereto.

The PGIS and DNA encoding same of the present invention are useful as reagents for
(1) the analysis of physicochemical property and biological property of PGIS at the molecular or genetic level,
(2) the analysis of the mechanism of regulating PGIS production and the mechanism of regulating $PGI_2$ production by PGIS, and
(3) the investigation of the cause of various cardiovascular diseases considered to be induced by the production imbalance between $PGI_2$ and $TXA_2$, and analysis at the molecular or genetic level for the development of therapeutic agent for said diseases.

In addition, they are useful as diagnostics for determining the in vivo tissue expression level and distribution of PGIS or mRNA thereof.

Moreover, they can be used as therapeutic agents for various cardiovascular diseases such as thrombosis, myocardial infarction, arteriosclerosis and angina pectoris, which increase the production level of $PGI_2$ based on lesion-specific introduction, into human and other animals, of PGIS, DNA encoding PGIS, fragment thereof or modified product thereof.

The expression system of PGIS comprising a recombinant vector containing DNA encoding the human-originated PGIS of the present invention, and a host cell transformed with said vector is useful for the production by genetic engineering, which enables easy and efficient mass production of human-originated PGIS.

In addition, the human-originated PGIS antibody of the present invention serves well for the purification of human-originated PGIS and the immunohistochemical analysis of the cause of a disease (specific staining of various tissues such as uterus, heart, skeletal muscle, lung and prostate).

The plasmid, enzyme such as restriction enzyme, T4DNA ligase and other substances to be used in Examples of the present invention are commercially available and can be used according to a conventional method. The procedures for cloning of cDNA, determination of nucleotide sequence, transfection of host cell, culture of transfectant, harvesting and purification of PGIS from obtained culture, and obtainment of antibody are well known to those skilled in the art, or can be known from literatures.

The pHPGIS36 (PBJT-BA-4, deposit number FERM BP-4653) and pHPGIS135 (PBJT-BA 5, deposit number FERM BP-4654) used in the present invention are at international deposit at National Institute of Bioscience and Human-Technology Agency of Industrial Science and Technology.

EXAMPLES AND REFERENCE EXAMPLES

The present invention is described detailedly in the following by way of Examples and Reference Examples, to which the present invention is not limited.

Example 1

Determination of cDNA nucleotide sequence
(1) Preparation of λ hPGIS141

Human genomic library (Genomic lung fibroblast cell line, W I 38, manufactured by Clone-Tech) was seeded at about $2 \times 10^5$ PFU, and screened by plaque hybridization using, as a probe, a bovine cDNA prepared in advance by the inventor (see Tanabe, T., Hara, S., Miyata, A., Brugger, R., and Ullrich, V. (1993) in Abstract book of 3rd international conference on eicosanoid and other bioactive lipids in cancer, inflammation and radiation Injury, p. 137).

As a result, four positive signals were obtained, one of which was isolated to a single plaque. Liquid culture thereof resulted in mass preparation of phage DNA. After purification, it was digested with various restriction enzymes, followed by mapping. A fragment comprising exon was identified by Southern hybridization, which was followed by structural analysis by DNA sequencing to confirm that the finally-isolated clone (λ hPGIS141) coded for human PGIS.

The λ hPGIS141 thus obtained was structurally analyzed by restriction enzyme site mapping and nucleotide sequence determination, and it was found that λ hPGIS141 contained the region corresponding to a 673rd–855th nucleotide sequence of bovine PGIS cDNA (SQ No. 8).

Based on the nucleotide sequence of λ hPGIS141 cDNA fragment thus obtained, primers [SQ No. 1: P1 primer (674–689), SQ No. 2: P2 primer (699–718), SQ No. 3: P3 primer (696–713), SQ No. 4: P4 primer (805–822)] having the sequences depicted in Sequence List SQ Nos. 1–4 were synthesized.

(2) Amplification of cDNA by PCR method

The 3'-downstream region and 5'-upstream region of cDNA were amplified by PCR method (Biochem. Biophys. Res. Commun. 178, 1479–1484 (1991)) using said primers and poly(A)+ RNA (mRNA) from 1 μg of human aorta vascular endothelial cells (hereinafter referred to as HAEC, manufactured by Kurabo) as a template.

For amplification of cDNA corresponding to the 3'-downstream region, cDNA was primed with a $dT_{17}$ adapter (5'-GACTCGAGTCGACATCGA-$(T)_{17}$-3', SQ No. 5), and elongated to give a first cDNA chain which was amplified with P1 primer (674–689) and the adapter primer (SQ No. 6), and then with P2 primer (699–718) and the adapter primer (SQ No. 6). The 5'-upstream region of the cDNA was amplified using a 5' RACE system (GIBCO BRL). According to the protocol, homomeric dC tail was added to the first cDNA chain and a second cDNA chain was formed using an adapter primer (5'-(CUA)4 GGCCACGCGTCGACTAGTACGGGIIGGGIIGGGIIG-3') (SQ No. 7). The fist step amplification was performed using P4 primer and the adapter primer (SQ No. 7). The second step amplification was performed using P3 primer and the adapter primer (SQ No. 7). The PCR method was repeated 35 cycles according to the following cycloprofile.

| Denaturation | 94° C., 1 minute |
| Annealing | 54° C., 1 minute |
| Elongation | 72° C., 3 minutes |

The respective PCR products (3'-downstream region amplification product and 5'-downstream region amplification product) were partially taken out and purified by electrophoresis using 1% agarose gel. Southern hybridization was applied using bovine cDNA (pBPGISI) as a probe, and DNA was extracted from the band which cross-hybridized to said probe. The obtained DNA was cloned into pBluescriptII SK(−).

That is, cloning and screening were performed by the following steps:
(1) cleaving out the band which showed a signal from a gel, after electrophoresis
(2) agarase digestion at 40° C. for one hour (agarase 1 unit/100 μl gel)
(3) extraction of DNA with phenol and subsequent ethanol precipitation (4) dissolving said DNA ethanol precipitate in sterile water and treating with polynucleotide kinase at 37° C. for one hour
(5) end repairing with Klenow fragment (16° C., 1 hr)
(6) ligation using Takara ligation kit
(7) transformation by a conventional method
(8) sewing in a plate
(9) forming a replica by a conventional method and
(10) colony hybridization of nitrocellulose filter of the replica by a conventional method, using bovine PGIS cDNA as a probe The hybridization was performed at 60° C. in 6×SSC [1×SSC containing 0.15M NaCl, 15 mM sodium citrate (pH 7.0)], 5×Denhardt's solution, 250 μg/ml salmon sperm DNA, 0.1% SDS and cDNA fragment ($10^6$ cpm/ml) labeled by random priming method. The filter obtained was washed twice with 3×SSC and 0.1% SDS at room temperature for 5 minutes and twice with 0.1×SSC and 0.1% SDS at 50° C. for 15 minutes. The filter was air-dried, and exposed to Fuji X ray film using a intensifying screen at −80° C. for 12–16 hr.

The obtained DNA insert was subcloned into pBluescriptII SK(−). By these steps, a clone (pHPGIS135) containing 3'-downstream region DNA of human-originated PGIS and a clone (pHPGIS36) containing 5'-upstream region DNA of human-originated PGIS were obtained. Then, the nucleotide sequence of the DNA insert of respective clones was determined by the Sanger method [Sanger, F., Nickle, S., and Coulson, A. R. (1977) Proc. Natl. Acad. Sci. USA 74, 5463–5467] using Taq dye primer cycle sequence kit (manufactured by Applied Biosystems) and Model 373A DNA sequencer (manufactured by Applied Biosystems). As a result, it was found that pHPGIS36 clone had, as a DNA insert sequence, a 740 bp nucleotide sequence (SQ No. 9) of cDNA of human PGIS, having an adapter sequence on the 9 side, based on which partial amino acid sequence of PGIS comprising 237 amino acid residues wherein ATG is the translation initiation sequence (Met) was identified.

Figure 2:
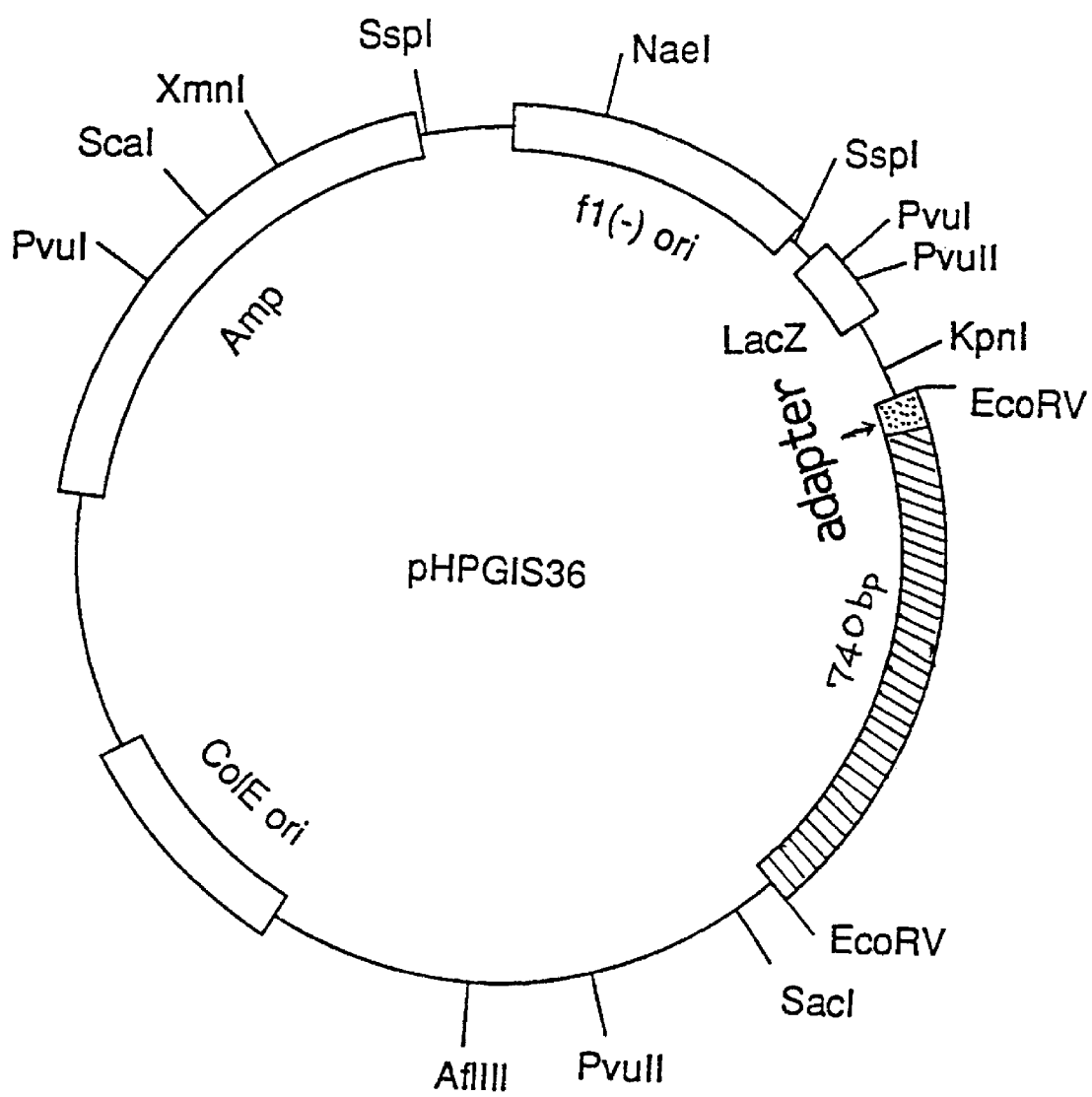
FIG. 2 shows a restriction enzyme map of plasmid pHPGIS36.
Figure 3:
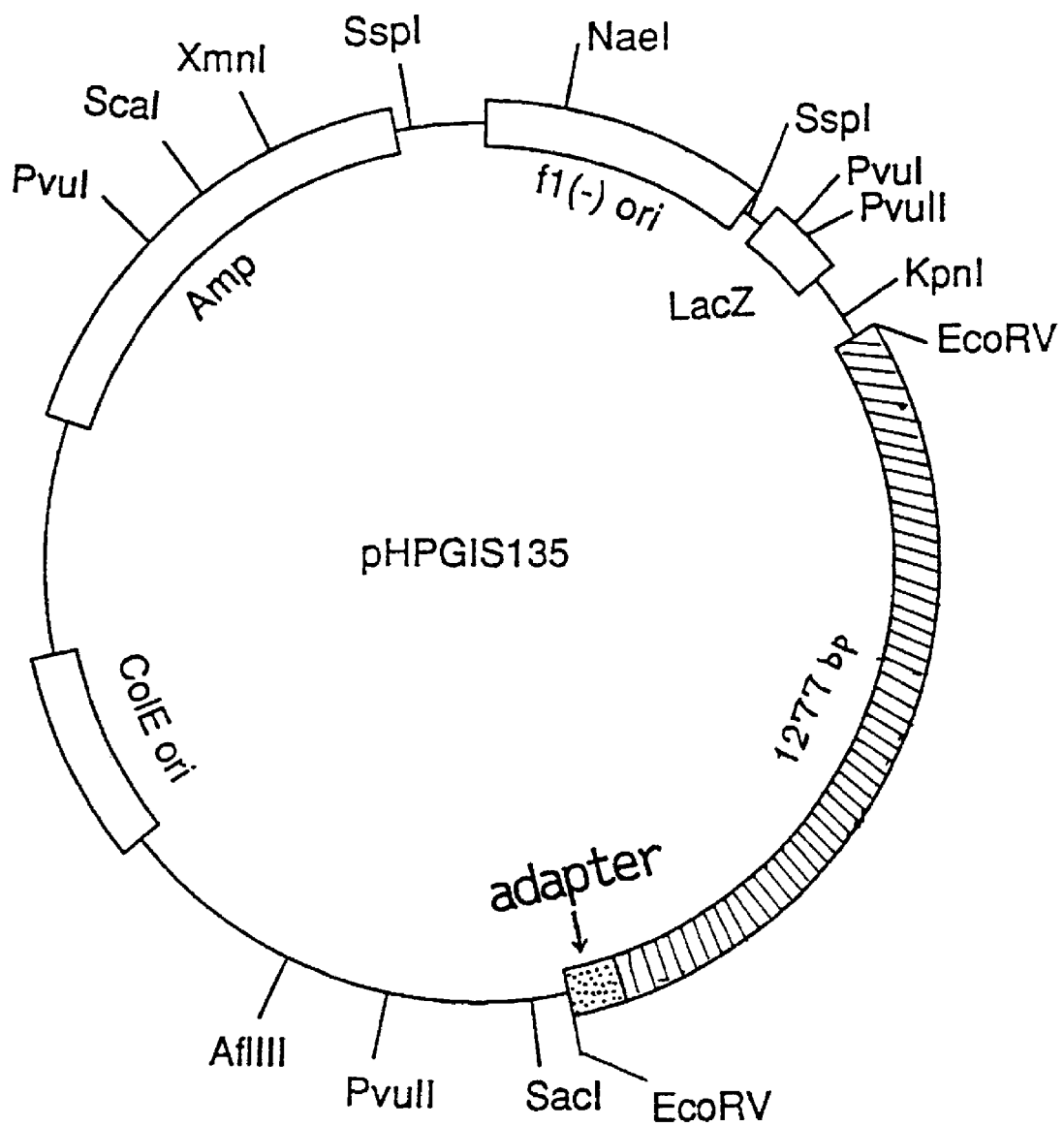
FIG. 3 shows a restriction enzyme map of plasmid pHPGIS135.

It was also found that pHPGIS135 clone comprised, as a DNA insert sequence, a 1277 bp nucleotide sequence (SQ No. 12) of cDNA of human PGIS, having an adapter sequence on the 3' side, based on which partial amino acid sequence of PGIS on the carboxyl side region starting from 226th aspartic acid was identified. The nucleotide sequence of human PGIS cDNA contained in pHPGIS36 clone and the amino acid sequence deduced therefrom are depicted in SQ No. 11 in the Sequence Listing to be mentioned later, and the nucleotide sequence of human PGIS cDNA contained in pHPGIS135 clone and the amino acid sequence deduced therefrom are depicted in SQ No. 13 therein. FIG. 1 shows a restriction enzyme map of human PGIS cDNA and the region of human PGIS cDNA, which corresponds to the DNA contained in λ hPGIS141, pHPGIS36 and pHPGIS135. FIG. 2 shows a restriction enzyme map of pHPGIS36 and FIG. 3 shows a restriction enzyme map of pHPGIS135.

Human PGIS cDNA obtained by the above-mentioned cloning had a consensus sequence of the initiation codon of eukaryotic shown by Kozak et al [Nucleic Acids Res. 12, 857–872 (1984)] at around the translation initiation codon, and TGA codon corresponding to the termination codon at 500 codons therefrom. Based on these facts, it was found that the cDNA of the cloned human PGIS comprised 1977 bp comprising 1500 bp encoding 500 amino acid residues, as shown in SQ No. 15, and the molecular weight of the protein coded thereby was speculated to be about 57,000.

Comparison of the amino acid sequence encoded by said DNA with the amino acid sequence of bovine-originated PGIS separately cloned by the present inventor revealed an about 88% homology. The study of bovine PGIS by the present inventor found that the bovine PGIS had a 31% homology with cholesterol 7α-hydroxylase belonging to the cytochrome P450 7 family (CYP7), and the region around the 441st Cys residue, which is heme-binding site (fifth ligand) of cytochrome P450, was reserved. The human PGIS similarly reserved the amino acid sequence corresponding to said region, and this region is considered to play an important role in the PGIS activity.

Although the bovine PGIS had a 31% homology with cholesterol 7α-hydroxylase, it had only a 16% homology with human thromboxane synthase belonging to the cytochrome P450 family and a not more than 40% homology with any of the known cytochrome P450 proteins. It is postulated, therefore, that it is a new family in the cytochrome P450 super family, and human PGIS also belongs to this new family.

A search for such structural correlation in activity is indispensable for the study and development of pharmaceutical products. Such search is accomplished only after the primary structure of human PGIS has been clarified. Accordingly, the present invention which discloses the primary structure of human PGIS for the first time is extremely important and significant for the research, and from industrial aspect as well.

Example 2
Expression of human PGIS
(1) Construction of expression vector for human PGIS A cDNA insert region is cleaved out respectively from the obtained pHPGIS36 clone and pHPGIS135 clone using a suitable restriction enzyme, and purified. The both fragments obtained were thermally denatured (95° C. for 10 minutes), followed by annealing. cDNA is replicated using a DNA polymerase to the both directions toward 5' and 3' from the overlapped region as the synthesis initiation region. Using the obtained whole length cDNA as a template, a primer is synthesized from each region of initiation codon or termination codon and PCR is performed. On this occasion, a suitable restriction enzyme site is constructed as an anchor site at 3' of the primer.

The PCR product thus obtained is purified, the nucleotide sequence of which is confirmed, and the product is digested with BamHI and SmaI (BglII) to give a BamHI-SmaI (BglII) fragment. Said BamHI-SmaI (BglII) fragment is introduced into the BamHI-SmaI site of pVL1393 expression vector previously treated with BamHI-SmaI. The recombinant plasmid thus formed (PGIS7) is characterized by restriction enzyme mapping and DNA sequence analysis.

(2) Baculovirus expression system

Sf9 cells (manufactured by In Vitrogen) are mono-layer cultured in a Grace's insect medium containing 10% fetal calf serum, 0.33% yeastolate and 0.33% lactoalbumin hydrolysate at 27° C. For the production of a recombinant virus, Sf9 cell ($1.5 \times 10^6$ cells) recombinant plasmid (PGIS7, 50 µg) and wild type baculovirus DNA (AcNPV; 1 µg) are mixed and transfected by calcium phosphate precipitation method. The recombinant baculovirus is isolated and amplified by a combination of plaque assay and slot hybridization using a $^{32}$P-labeled cDNA fragment of PGIS as a probe.

Said Sf9 cells are infected with wild type baculovirus or recombinant baculovirus. At 3 days after the infection, cells are collected ($2 \times 10^8$ cells) and incubated for 5 hours in a serum-containing medium with or without 10 µM hemin.

The obtained cells are washed with phosphate-buffered saline and preserved at −80° C. The microsomal fraction of the cell is prepared according to the method of Haurand and Ullrich et al. [(J. Biol. Chem. 260, 15059–15067) (1985)]. The obtained cells ($2 \times 10^8$ cells ) are homogenized in a solution (20 ml) of 10 mM potassium phosphate buffer (pH 7.0), 10 mM EDTA, 5 mM glucose, 0.1 mM dithiothreitol (DTT), 1.15% KCl, 2 µg/ml leupeptin, 2 µg/ml pepstatin, 10 µg/ml soybean trypsin inhibitor and 44 µg/ml phenylmethylsulfonyl fluoride, and subjected to ultrasonication (30 seconds, 4 times) using a Branson sonifier model 450.

The obtained homogenate is centrifuged at 7,000×g for 15 minutes, and the obtained supernatant is centrifuged at 105,000×g for 60 minutes. The sediment obtained is suspended in 10 mM potassium phosphate buffer (3 ml, pH 7.0) containing 20% glycerol, 1 mM DTT and 1 mM EDTA by sonication. The protein concentration is determined by Lowry method using bovine serum albumin as a standard, and a solution for immunoblot analysis and PGIS assay at 5 mg/ml is prepared.

(3) Western immunoblot analysis

The infected Sf9 cells and human platelet microsomal fraction are subjected to 10% SDS-PAGE according to the method of Laemmli [Nature 227, 680–685 (1979)]. The migrated protein is electrophoretically transferred onto a polyvinylidene difluoride (PVDF) membrane (Immobilon, Millipore) according to the method of Towbin et al. [Proc. Natl. Acad. Sci. USA 76,4350–4354 (1979)]. Tris-HCl buffered saline (TBS) (pH 7.4) containing 10% equine serum is pretreated at room temperature for 30 minutes, and the blot membrane is incubated with polyclonal antibody against bovine PGIS in TBS containing 3% skim milk.

After washing with TBS containing 0.05% Tween 20, the membrane is incubated in TBS containing 3% skim milk at 37° C. for 30 minutes together with anti-mouse IgG equine antibody conjugated with horseradish peroxidase (manufactured by Vector Laboratories). After thorough washing with TBS containing 0.05% Tween 20, the band showing positive immunological response is detected using an immunostaining HRP kit (manufactured by Konica).

Figure 4:
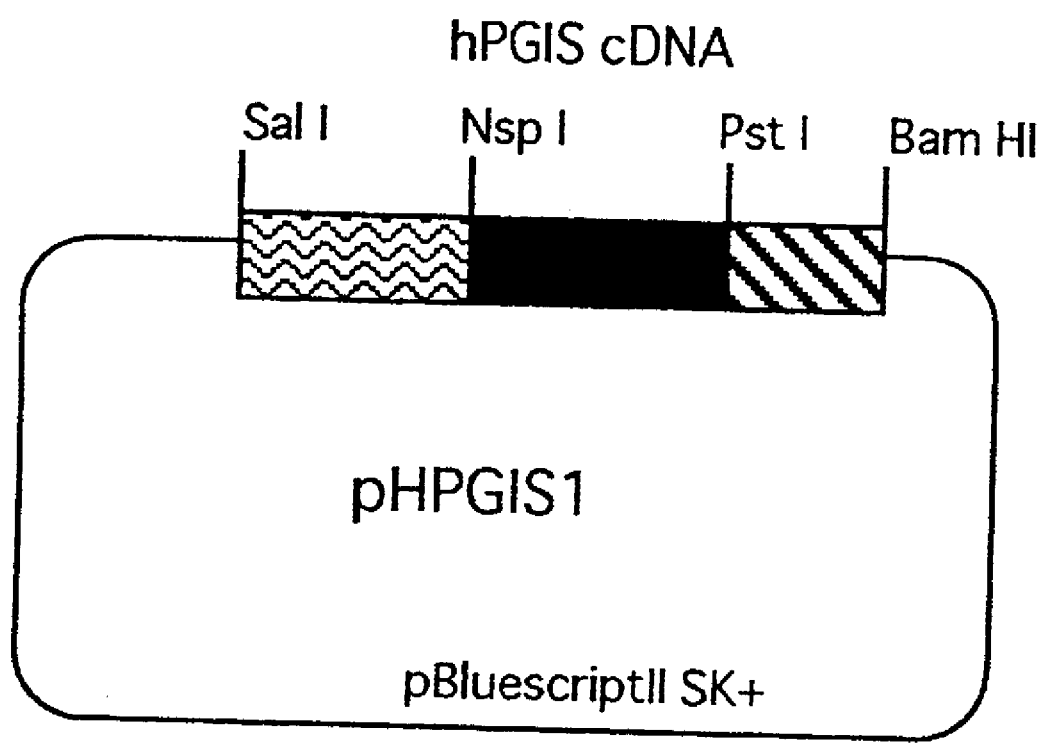
FIG. 4 shows a restriction enzyme map of plasmid pHPGIS1.

Example 3
Expression of human PGIS in cultured animal cell
(1) Preparation of whole length human PGIS cDNA The obtained pHPGIS36 clone was cleaved out with restriction enzymes SalI and NspI and purified to give a SaLI-NspI fragment. The pHPGIS135 clone was cleaved out with restriction enzymes PstI and BamHI and purified to give a PstI-BamHI fragment. Furthermore, primers [SQ No. 16: P5 primer (676–699), SQ No. 17: P6 primer (832–855)] having sequences depicted in Sequence Listing Sequence Nos. 16 and 17 were synthesized based on the nucleotide sequence of λ hPGIS141. Using these primers and λ hPGIS141 as a template, a middle stream region of human PGIS cDNA was amplified by PCR method, cleaved with restriction enzymes NspI and PstI, purified and confirmed for the nucleotide sequence and used as an NspI-PstI fragment. These SalI-NspI fragment, PstI-BamHI fragment and NspI-PstI fragment were bound and introduced into the SalI-BamHI site of pBluescriptII SK+ (manufactured by STRATAGENE) previously treated with SalI-BamHI, whereby a plasmid (pHPGIS1) containing the whole length human PGIS cDNA was prepared. FIG. 4 shows the restriction enzyme map of pHPGIS 1.

(2) Construction of human PGIS expression vector for cultured animal cell

Human PGIS cDNA insert region was cleaved out from the obtained pHPGIS1 clone with restriction enzymes SalI and BamHI and purified to give a SalI-BamHI fragment. This SalI-BamHI fragment was introduced into the SalI-BamHI site of pCMV7 expression vector [supplied by Dr.

Figure 5:
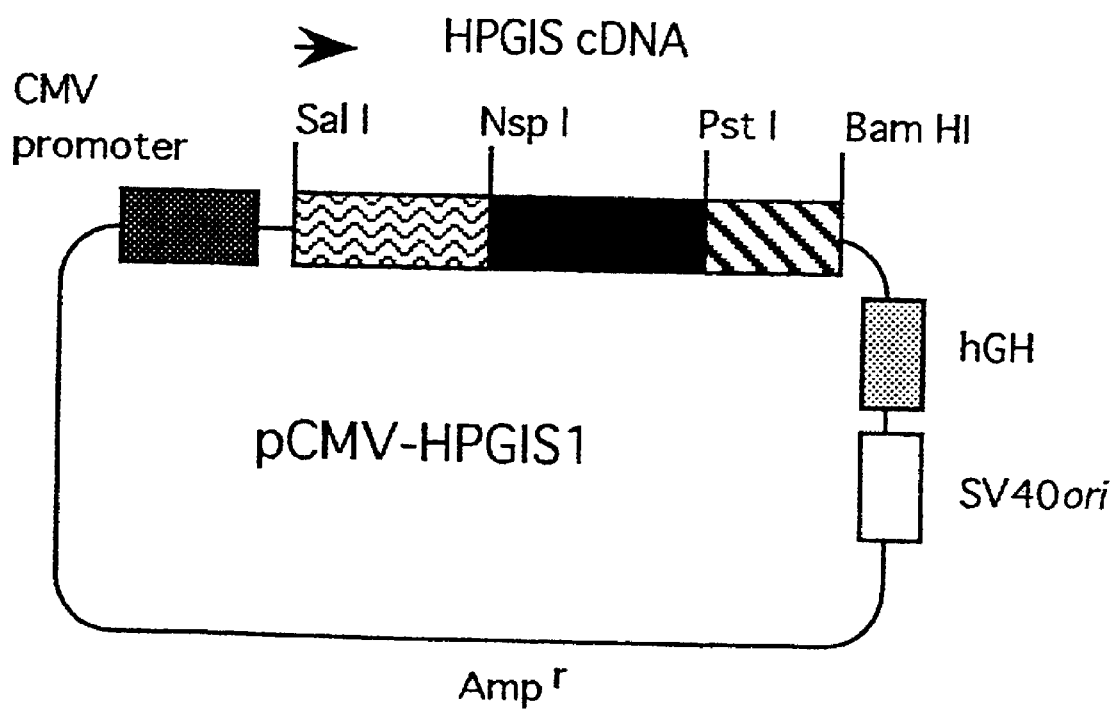
FIG. 5 shows a restriction enzyme map of human PGIS expression vector pCMV-HPGIS1.

David W. Russel, University of Texas Southwestern Medical Center, Cell, 75, 187–197 (1993); J. Biol. Chem., 264, 8222–8229 (1989)] previously treated with SalI-BamHI, whereby a human PGIS expression vector (pCMV-HPGIS 1) for cultured animal cell was prepared. FIG. 5 shows the restriction enzyme map of pCMV-HPGIS 1.

(3) Expression of human PGIS in cultured animal cell

Human fetus kidney-derived 293 cells (manufactured by Dainippon Pharmaceutical Co., Ltd.) were sewn in a 60 mm dish at $3\times10^5$ cells, and mono-layer cultured at 37° C. for 24 hours in Dulbecco modified Eagle's medium (DMEM) containing 10% fetal calf serum, 100 U/ml penicillin and 100 μg/ml streptomycin. Then, a recombinant plasmid (pCMV-HPGIS 1, 3 μg) and pVA1 [adenovirus VA1 gene, 3 μg: supplied by Dr. David W. Russel, University of Texas Southwestern Medical Center, Mol. Cell. Biol., 7, 549–551 (1987)] were mixed and transfected by lipofectin method (GIBCO BRL). At 40 hours after the transfection, the cells were washed with phosphate-buffered saline and collected. The cells were suspended in 10 mM calcium phosphate buffer (pH 7.0) containing 10 mM EDTA, 10 mM phenyl-methanesulfonyl fluoride (PMSF), 5 mM glucose, 0.1 mM dithiothreitol (DTT), 1.15% KCl, 2 μg/ml leupeptin, 2 μg/ml pepstatin and 10 μg/ml soybean trypsin inhibitor, and subjected to ultrasonication (10 seconds, 10 times) using ASTRASON™ Model XL2020.

Figure 7:
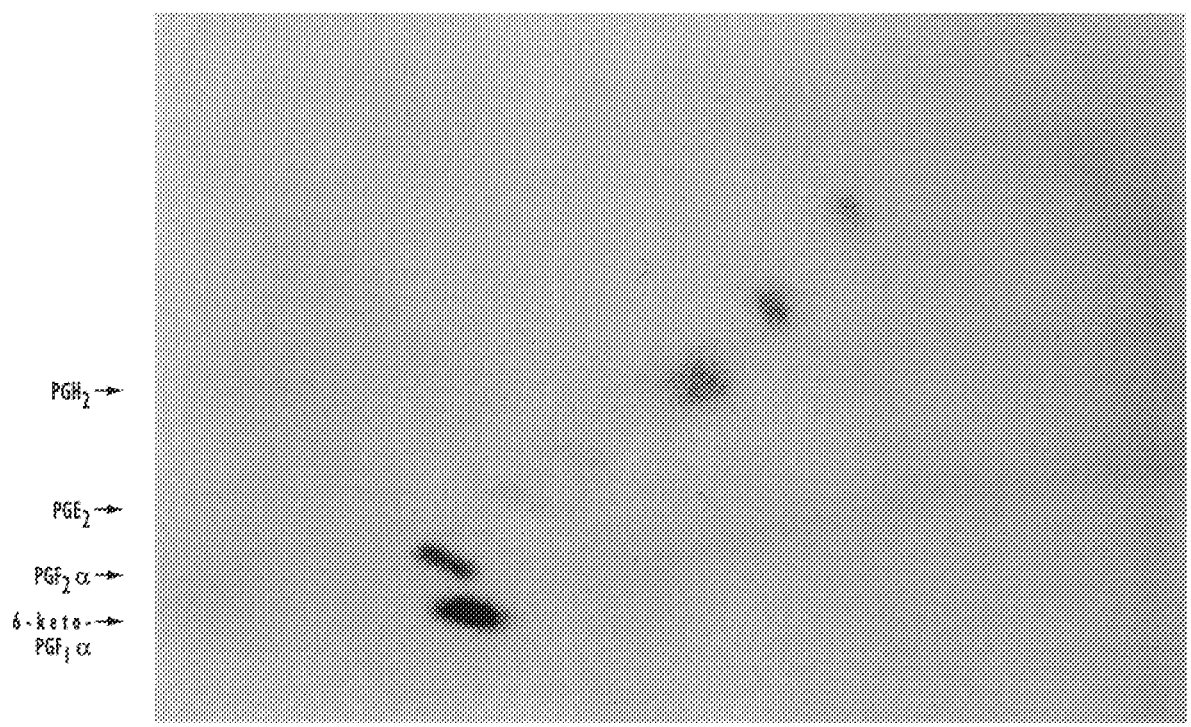
FIG. 7 is a photograph showing the results of the analysis, by thin layer chromatography, of the PGIS activity in the cells into which pCMV-HPGIS1 has been introduced.
Figure 8:
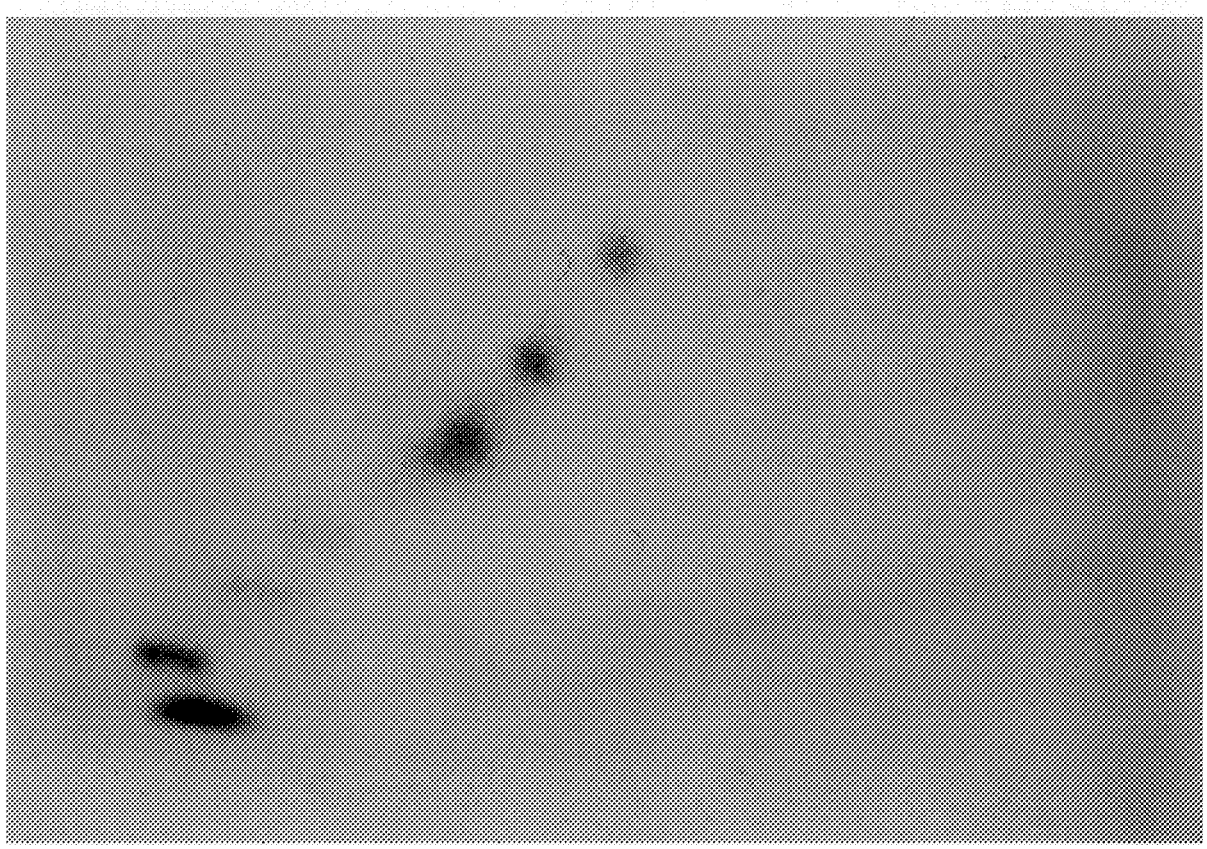
FIG. 8 is a photograph showing the results of the analysis, by thin layer chromatography, of the PGIS activity in positive control (bovine platelet microsomes).
Figure 9:
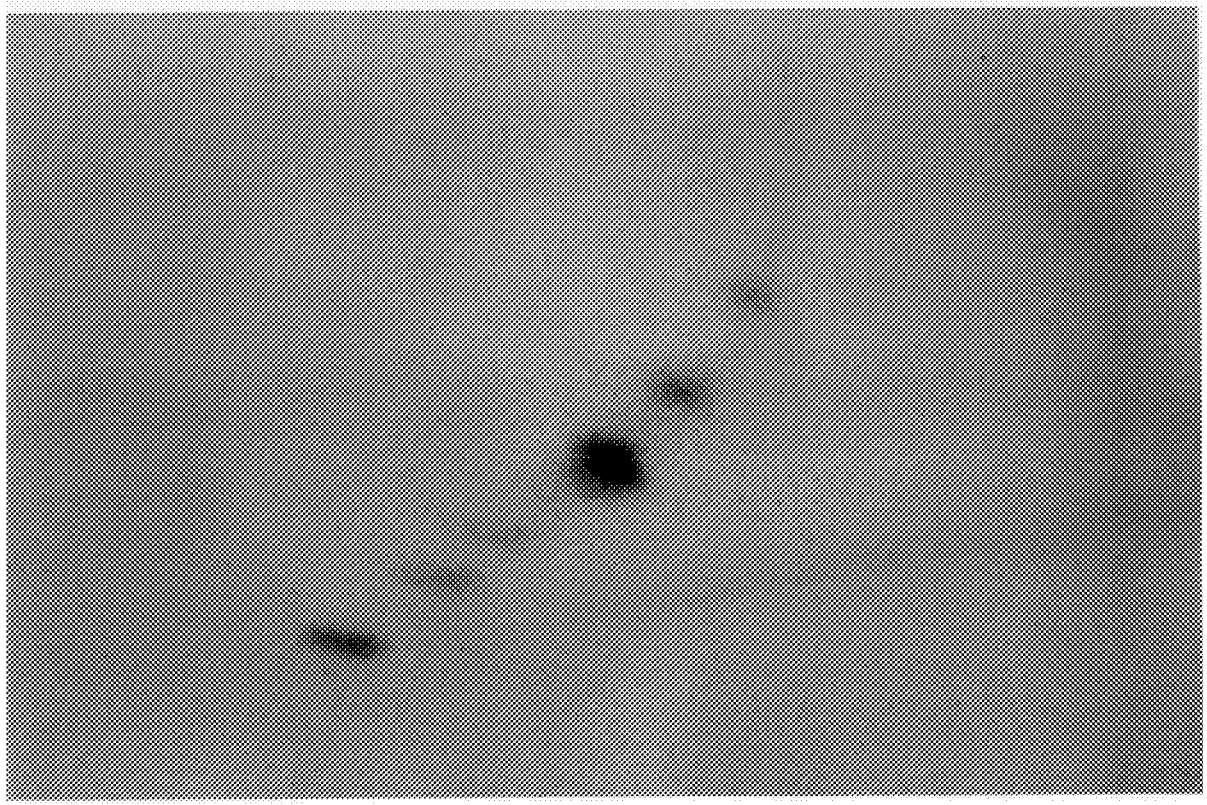
FIG. 9 is a photograph showing the results of the analysis, by thin layer chromatography, of negative control wherein pCMV alone was introduced.

The obtained homogenate was centrifuged at 100,000×g for 60 minutes and the obtained sediment was suspended in 10 mM calcium phosphate buffer (pH 7.0) containing 1 mM EDTA, 1 mM PMSF, 20% glycerol and 0.1 mM DTT. The protein concentration of the obtained sample was determined using a BCA (bicinchoninic acid) protein concentration determination kit (manufactured by PIERCE) using bovine serum albumin as a standard. The PGIS activity of the obtained sample was determined by reacting same with $^{14}C$-labeled $PGH_2$ (5 nmole) as a substrate at 24° C. for 2 minutes, separating 6-keto-$PGF_1\alpha$, which is a metabolite of the produced $PGI_2$, by thin layer chromatography, and detecting the radioactivity of the 6-keto-$PGF_1\alpha$. FIG. 7 shows the detected PGIS activity, FIG. 8 shows PGIS activity of positive control (bovine platelet microsomes) and FIG. 9 shows the analysis results, by thin layer chromatography, of negative control wherein pCMV7 alone was introduced.

As the result of the determination using a sample prepared from the cell into which an expression vector incorporating human PGIS cDNA had been introduced, a spot of 6-keto-$PGF_1\alpha$, which is a metabolite of $PGI_2$, was detected as shown by an arrow in FIG. 7. The results were the same as those obtained using bovine platelet microsome containing PGIS as a positive control (FIG. 8). In contrast, the determination using a sample prepared from the cell into which an expression vector without human PGIS cDNA had been introduced failed to detect a spot of 6-keto-$PGF_1\alpha$. The spot of $PGH_2$ was thicker (FIG. 9) than in FIG. 7 and FIG. 8. The above results mean that PGIS cDNA incorporated in the expression vector was expressed as a recombinant protein (recombinant PGIS) having PGIS activity and this protein acted on $PGH_2$ to produce 6-keto-$PGF_1\alpha$ which is a metabolite of $PGI_2$.

Example 4

Expression of human PGIS in cultured animal cell

Figure 6:
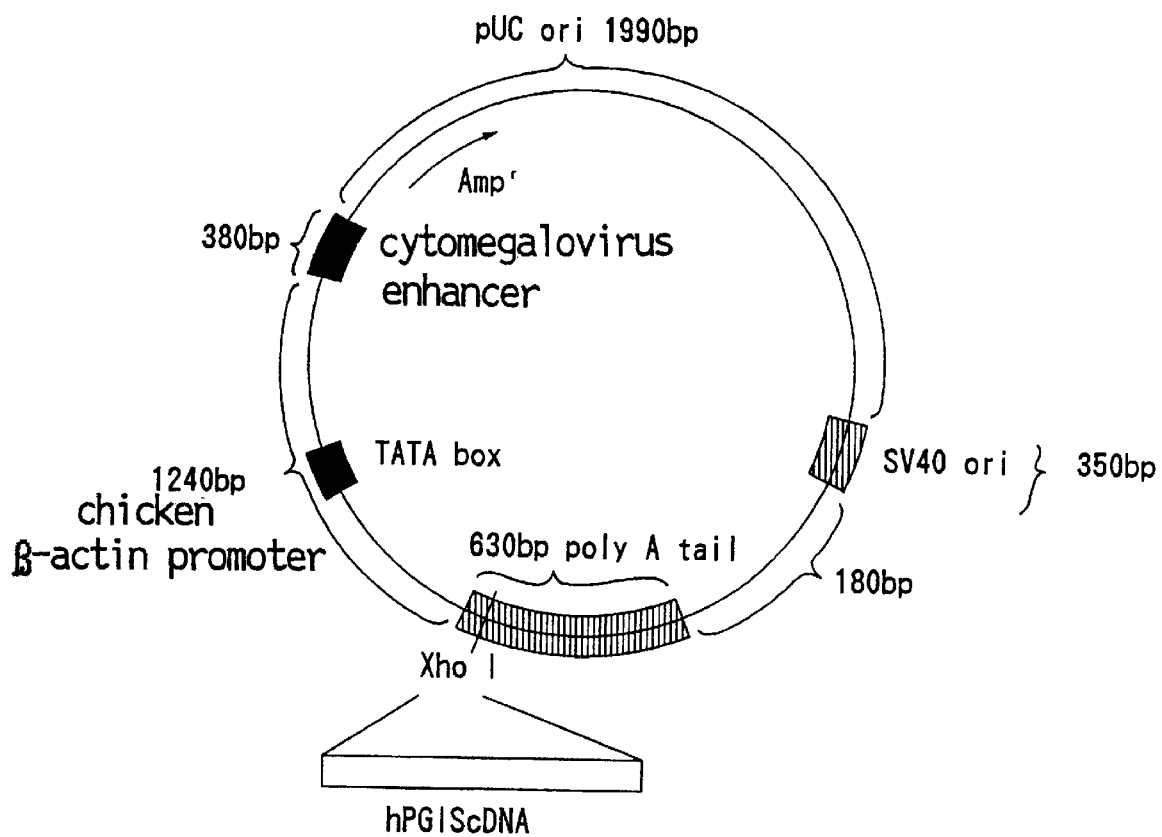
FIG. 6 shows an expression vector pUC-CAGGS.

Human PGIS cDNA was bound to the XhoI site of the expression vector pUC-CAGGS [having an enhancer of cytomegalovirus and chiken β-actin promoter] as shown in FIG. 6 [prepared according to the description in Gene 108, 193–200 (1991)] to construct an expression vector. Two kinds of vectors, i.e., this vector and a vacant vector without human PGIS cDNA, were introduced into vascular smooth muscle cells respectively prepared from rat aorta by HVJ-liposome method [Hypertension 21, 894–899 (1993)] and incubated in a serum-free medium [Dulbecco modified Eagle's medium (DMEM) containing $5\times10^{-7}M$ insulin, 50 μg/ml transferin, 0.2 mM ascorbic acid, 100 U/ml penicillin and 100 μg/ml streptomycin] in a $CO_2$ incubator at 37° C. for 2 days. Then, the medium was changed to a medium containing 1% or 5% fetal calf serum (FCS), and $^3H$-thymidine was added 16 hours later. At 8 hours after the addition of thymidine, the thymidine uptake was determined by a conventional method [Cancer Immunol. Immunother. 24, 158–164 (1987)].

Figure 10:
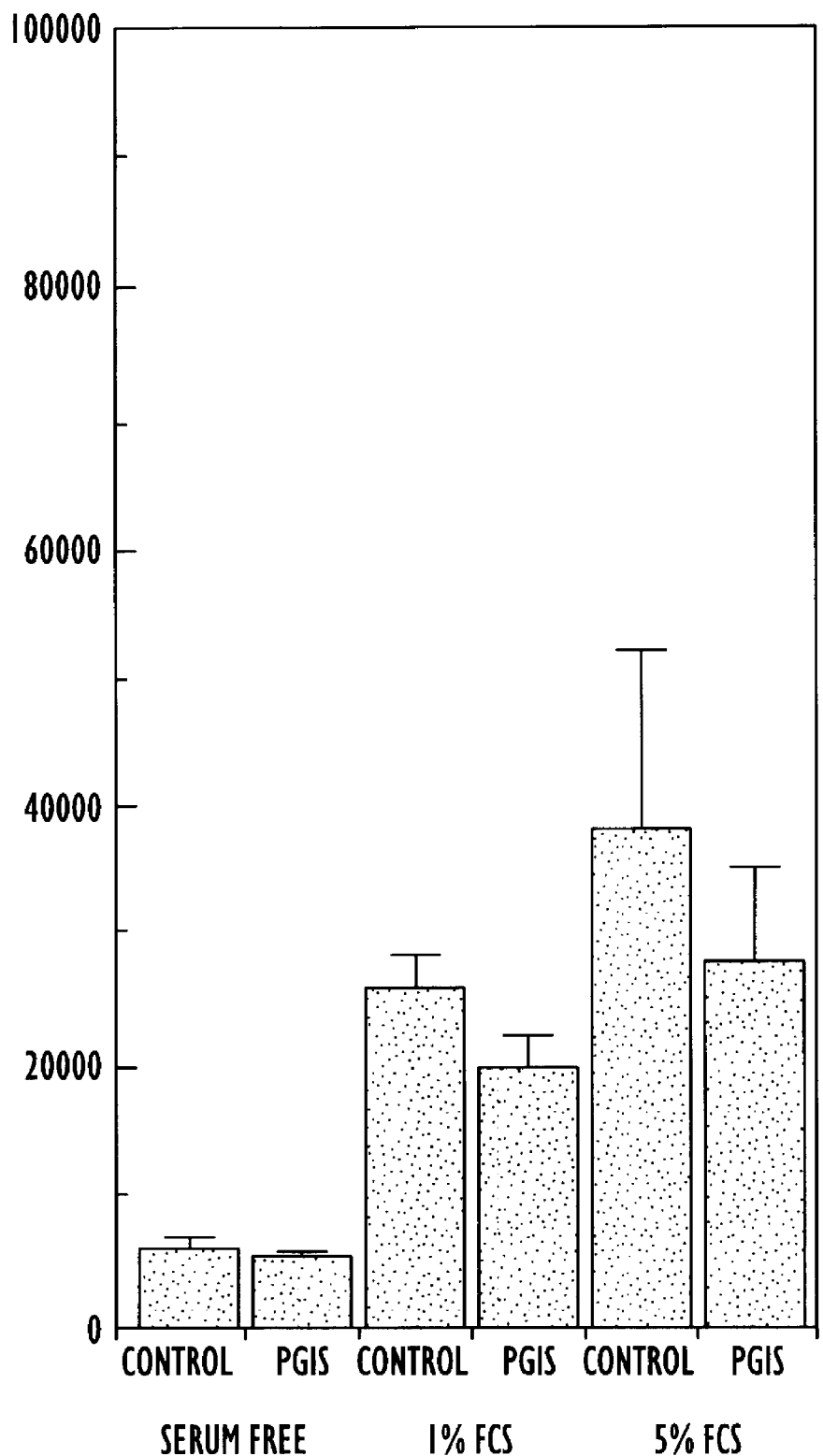
FIG. 10 is a graph showing the effects of the introduction of human PGIS expression vector on the blood vessel smooth muscle cell proliferation.

The results are shown in FIG. 10, wherein control was a cell into which a vacant vector was introduced and PGIS was a cell into which an expression vector bound with human PGIS cDNA was introduced.

Addition of serum to the vascular smooth muscle cell cultured in the absence of serum led to a promoted proliferation which increased thymidine uptake. In the vascular smooth muscle cell into which an expression vector ligated with human PGIS cDNA was introduced, thymidine intake, namely, proliferation, was significantly suppressed as compared to the cell into which a vacant vector was introduced. This result suggests the possibility of PGIS cDNA introduction suppressing abnormal growth of smooth muscle cells in vascular intima which is observed in arteriosclerosis and the like.

Example 5

Preparation of anti-PGIS polyclonal antibody

PGIS dissolved in 0.5 ml of phosphate-buffered saline (PBS) and an equivalent amount of adjuvant were emulsified and subcutaneously injected to rabbit. Thereafter, similar subcutaneous injection was given twice every 10 days, and blood was taken from the rabbit 10 days after the final subcutaneous injection. Anti-PGIS/IgG was purified and obtained from rabbit anti-PGIS serum prepared from the blood of said rabbit using protein A sepharose 4B (Bio-Rad).

Example 6

Preparation of anti-PGIS monoclonal antibody

① Mouse

Male inbred line BALB/c mice (5 weeks of age) were obtained and bred on standard pellet in an animal breeding chamber (23°+1° C., 70% humidity) with optional watering.

② Immunogen

Human-originated purified PGIS was used. The human PGIS was prepared to a concentration of 1 mg/ml with Dulbecco PBS, dispensed into test tubes by 100 μg and freeze-preserved at −80° C. until use.

③ Immunizing method

Human PGIS 100 μg/0.5 ml and an equivalent amount of Freund's complete adjuvant were mixed. An emulsified antigen (20 μg) was administered to five male BALB/c mice (5 weeks of age) intraperitoneally and subcutaneously at dozen sites on the back every 2 weeks for 2 months. After the immunization for 2 months, antibody titer was measured, and the mice having high antibody titer were picked and applied with additional intraperitoneal administration of 50 μg, 100 μg or 200 μg thereof every other week.

After the immunization for 2 months, two different mice were intraperitoneally administered with 100 μg thereof after a blank of one month. One week later, 100 μg thereof was intravenously injected for additional immunization.

④ Cell fusion

At 3 days from the final immunization, the spleen of the BALB/c mice was removed to prepare suspensions of spleen cells in EMEM culture medium. The spleen cells were washed 4 times with EMEM culture medium and counted.

For cell fusion, 2-amino-6-oxy-8 azapuraine (8-Azaguanine)-resistant BALB/c mouse myeloma-derived cultured cell line (P3-X63-Ag8.653, hereinafter abbreviated as X63 cells) was used as a parent cell line. The X63 cells were subcultured in RPMI-1640 culture medium (20 μg/ml, containing 8-Azaguanine) supplemented with 5% inactivated fetal calf serum (FCS), and X63 cells in the logarithmic growth phase were washed 3 times with RPMI-1640 culture medium and counted.

Cell fusion is performed in RPMI-1640 culture medium containing polyethylene glycol 4000 at a concentration of 50 (w/v) %.

That is, spleen cells and X63 cells are mixed at a ratio of 10:1 and centrifuged at 1500 rpm for 5 minutes. Supernatant is removed, and cell pellets are thoroughly suspended and subjected to cell fusion according to the method of Kohler and Milstein using polyethylene glycol. Thereafter, the spleen cells are suspended in an HAT selective medium (10% FCS-added RPMI-1640 culture medium containing $1\times10^{-4}$M hypoxanthine, $4\times10^{-7}$M aminopterin and $1.6\times10^{-5}$M thymidine) so that the spleen cells are contained at a concentration of $3.5\times10^6$ cells/ml. Then, the cell suspension is dispensed into each well of 96 well microtest plate by 100 μl and cultured in a carbonic acid gas incubator (37° C., 95% humidity, 8% carbonic acid gas). On day 1 and day 2 after the initiation of culture, HAT medium is added by one drop to each well and by 2 drops on day 7 and day 9 after the initiation of incubation, which is followed by further culture.

⑤ Screening

From 10 days after the initiation of culture, clone cells emerge. For confirmation of antibody production, hybridoma culture supernatant is subjected to an antigen-antibody reaction test.

That is, 50 μl each from hybridoma culture supernatant and human PGIS antigen liquid is placed in a U-bottomed microtiter plate and thereto is added 50 μl of 20% suspension of Sepharose 4B bound with anti-mouse immunoglobulin antibody. The mixture is stirred at room temperature for one hour and left standing for 10 minutes. After confirmation of complete sedimentation of anti-mouse immunoglobulin antibody-bound Sepharose 4B on the bottom of the well, 20 μl of the supernatant is taken and determined for concentration of residual human PGIS in the supernatant by PGIS ELISA system. When anti-human PGIS monoclonal antibody against human PGIS is present in the hybridoma culture supernatant, human PGIS and anti-human PGIS monoclonal antibody react and anti-mouse immunoglobulin antibody-bound Sepharose 4B sediment is formed as an antigen-antibody complex to decrease the concentration of residual human PGIS in the supernatant, thus proving the presence of anti-human PGIS monoclonal antibody.

Reference Example 1

RNA blot analysis

RNA blot hybridization analysis was made to examine the influence of several kinds of cytokines on the expression of HAEC-derived human PGIS mRNA.

The entire RNA (30 μg) derived from each HAEC which was incubated for 24 hours with several kinds of cytokines [IL-1α (1 ng/ml), IL-1β (1 ng/ml), IL-6 (2.5 ng/ml), TNF-α (5 ng/ml) and TNF-β (1 ng/ml)] was denatured with formamide, electrophoresed on 1% agar gel containing 1.5% formaldehyde, and transferred onto a nylon membrane. A probe [pHPGIS 135 and glyceraldehyde-3-phosphate dehydrogenase (GAPDH)] was labeled with [α-$^{32}$P]dCTP by random priming method [Feinberg, A. P., and Vogelstein, B. (1983) Anal. Biochem. 132, 6–13].

Figure 11:
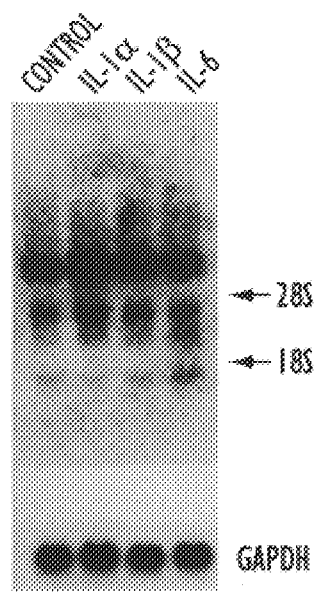
FIG. 11 is a photograph showing the results of RNA blot (electrophoresis) analysis of human pGIS mRNA treated with cytokines.

Then, hybridization was applied according to the method described in Biochem. Biophys. Res. Commun. 178, p 1479–1484 (1991). The membrane obtained was washed with 0.1×SSC (0.15M NaCl, 0.015M sodium citrate, pH 7.0) containing 0.1% SDS at 60° C., air-dried and autoradiographed. The results are shown in FIG. 11. The main band of the HAEC-derived human PGIS mRNA was found at about 6 kb and three other minor bands were found (3.2, 2.5 and 1.7 kb). The test results revealed that the expression of human PGIS mRNA incubated for 24 hours with IL-1α, IL-1β or IL-6 increased about 2-fold as compared with the control without cytokine treatment. Accordingly, increase in $PGI_2$ production caused by cytokine is considered to be attributable to the increased expression and production of PGIS which was achieved by cytokine. Thus, the treatment with cytokine is an extremely useful method for increasing PGIS expression to increase PGIS activity, which in turn accelerates $PGI_2$ production.

Reference Example 2

In vivo distribution of PGIS mRNA

RNA blot analysis was made to examine the distribution of PGIS mRNA expression in human body. Specifically, a filter was purchased from Clone-Tech on which poly (A)$^+$ RNA of various human tissues was electrophoresed and blotted. hPGIS135 was labeled with $^{32}$P by the aforementioned method and subjected to Northern blot hybridization under the same conditions as above.

Figure 12:
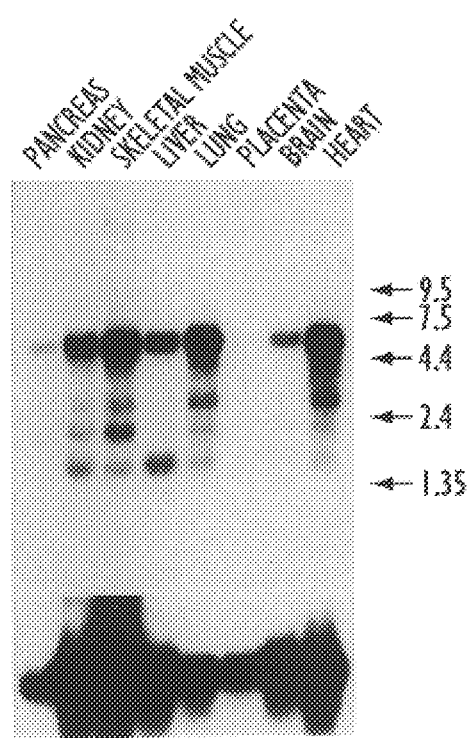
FIG. 12 is a photograph showing the distribution of PGIS mRNA expression in human body (pancreas, kidney, skeletal muscle, liver, lung, placenta, brain and heart) by electrophoresis.

The results are shown in FIG. 12 and FIG. 13. The results confirm that PGIS mRNA was abundantly expressed widely in human tissues, particularly, in uterus, heart, skeletal muscle, lung and prostate and at significant levels, though slightly, in small intestine, kidney, liver and brain. These results coincide with the conventional reports of enzymatic activity and distribution in tissue of immunological response of PGIS, thus suggesting various biological roles assumed by PGIS besides the action in the vascular system. The 6 kb main, strong band and 3 weak bands as shown in FIG. 11 were observed in all tissues mentioned above, though relative thickness among the weak bands varied between tissues. Such various modes of presence of transcription products suggest possible different splicing of mRNA or the presence of an analogous gene (isozyme) as found in prostaglandin endoperoxidase.

What is claimed is:

1. An isolated DNA comprising a DNA having a nucleotide sequence encoding an amino acid sequence of a human-originated prostacyclin synthase depicted in Sequence Listing, Sequence No. 15.

2. The DNA of claim 1, comprising a DNA having a 28th–1527th nucleotide sequence shown in Sequence Listing, Sequence No. 14.

3. The DNA of claim 2, comprising a DNA having a 28th–1527th nucleotide sequence shown in Sequence Listing, Sequence No. 14.

4. An isolated polypeptide comprising an amino acid sequence of a human-originated prostacyclin synthase shown in Sequence Listing, Sequence No. 15.

5. The polypeptide of claim 4, comprising an amino acid sequence of a human-originated prostacyclin synthase shown in Sequence Listing, Sequence No. 15.

6. A recombinant vector comprising the DNA of any one of claims 1 to 3.

7. A host cell transformed with the recombinant vector of claim 6.

8. A transformed cell identified by International Deposit No. FERM BP-4653 or FERM BP-4654.

9. A method for preparing a human-originated prostacyclin synthase, comprising culturing the host cell of claim 7 in a medium and recovering a human-originated prostacyclin synthase from the obtained culture.

10. A pharmaceutical composition comprising the DNA of any one of claims 1 to 3 and a pharmaceutically acceptable carrier.

11. A pharmaceutical composition comprising the recombinant vector of claim 6 and a pharmaceutically acceptable carrier.

12. A pharmaceutical composition for promoting prostaglandin $I_2$ production, comprising the DNA of any one of claims 1 to 3 and a pharmaceutically acceptable carrier.

13. A pharmaceutical composition for promoting prostaglandin $I_2$ production, comprising the recombinant vector of claim 6 and a pharmaceutically acceptable carrier.

14. A pharmaceutical composition for treating a disease induced by a low production of prostaglandin $I_2$, comprising the DNA of any one of claims 1 to 3 and a pharmaceutically acceptable carrier.

15. A pharmaceutical composition for treating a disease induced by a low production of prostaglandin $I_2$, comprising the recombinant vector of claim 6 and a pharmaceutically acceptable carrier.

16. A method for promoting prostaglandin $I_2$ production, comprising introducing the DNA of any one of claims 1 to 3 into a human or an animal.

17. A method for promoting prostaglandin $I_2$ production, comprising introducing the recombinant vector of claim 6 into a human or an animal.

18. A method for treating a disease induced by a low production of prostaglandin $I_2$, comprising introducing the DNA of any one of claims 1 to 3 into a human or an animal.

19. A method for treating a disease induced by a low production of prostaglandin $I_2$, comprising introducing the recombinant vector of claim 6 into a human or an animal.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "PRIMER/SYNTHETIC DNA"

( x i ) SEQUENCE DESCRIPTION: SEQ ID NO:1:

GGGACAAGGA CCACAT                                                                                  16

( 2 ) INFORMATION FOR SEQ ID NO:2:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "PRIMER/SYNTHETIC DNA"

( x i ) SEQUENCE DESCRIPTION: SEQ ID NO:2:

CAAAAGTCGC CTGTGGAAGC                                                                              20

( 2 ) INFORMATION FOR SEQ ID NO:3:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "PRIMER/SYNTHETIC DNA"

( x i ) SEQUENCE DESCRIPTION: SEQ ID NO:3:

CACAGGCGAC TTTTGACA                                                                                18

( 2 ) INFORMATION FOR SEQ ID NO:4:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "PRIMER/SYNTHETIC DNA"

( x i ) SEQUENCE DESCRIPTION: SEQ ID NO:4:

TGCCTGCATC TCCTCTGA                                                                                18

( 2 ) INFORMATION FOR SEQ ID NO:5:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear (i i) MOLECULE TYPE: other nucleic acid
    (A) DESCRIPTION: /desc = "PRIMER/SYNTHETIC DNA"

(x i) SEQUENCE DESCRIPTION: SEQ ID NO:5:

GACTCGAGTC GACATCGATT TTTTTTTTTT TTTTT                                    35

(2) INFORMATION FOR SEQ ID NO:6:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (i i) MOLECULE TYPE: other nucleic acid
      (A) DESCRIPTION: /desc = "PRIMER/SYNTHETIC DNA"

(x i) SEQUENCE DESCRIPTION: SEQ ID NO:6:

GACTCGAGTC GACATCG                                                         17

(2) INFORMATION FOR SEQ ID NO:7:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (i i) MOLECULE TYPE: other nucleic acid
      (A) DESCRIPTION: /desc = "PRIMER/SYNTHETIC RNA"

(x i) SEQUENCE DESCRIPTION: SEQ ID NO:7:

CUACUACUAC UAGGCCACGC GTCGACTAGT ACGGGNNGGG NNGGGNNG                      48

(2) INFORMATION FOR SEQ ID NO:8:

(i) SEQUENCE CHARACTERISTICS:
      (A) LENGTH: 183 base pairs
      (B) TYPE: nucleic acid
      (C) STRANDEDNESS: double
      (D) TOPOLOGY: linear (i i) MOLECULE TYPE: cDNA (v i) ORIGINAL SOURCE:
      (A) ORGANISM: Homo sapiens
      (B) STRAIN: lambda hPGIS141

(i x) FEATURE:
      (A) NAME/KEY: CDS
      (B) LOCATION: 1..183

(x i) SEQUENCE DESCRIPTION: SEQ ID NO:8:

GGG GAC AAG GAC CAC ATG TGC AGT GTC AAA AGT CGC CTG TGG AAG CTG           48
Gly Asp Lys Asp His Met Cys Ser Val Lys Ser Arg Leu Trp Lys Leu
 1               5                  10                  15

CTA TCC CCA GCC AGG CTG GCC AGG CGG GCC CAC CGG AGC AAA TGG CTG           96
Leu Ser Pro Ala Arg Leu Ala Arg Arg Ala His Arg Ser Lys Trp Leu
             20                  25                  30

GAG AGT TAC CTG CTG CAC CTG GAG GAG ATG GGT GTG TCA GAG GAG ATG          144
Glu Ser Tyr Leu Leu His Leu Glu Glu Met Gly Val Ser Glu Glu Met
         35                  40                  45

CAG GCA CGG GCC CTG GTG CTG CAG CTG TGG GCC ACA CAG                      183
Gln Ala Arg Ala Leu Val Leu Gln Leu Trp Ala Thr Gln
     50                  55                  60

(2) INFORMATION FOR SEQ ID NO:9:

(i) SEQUENCE CHARACTERISTICS:

(A) LENGTH: 61 amino acids
(B) TYPE: amino acid
(D) TOPOLOGY: linear (ii) MOLECULE TYPE: protein (xi) SEQUENCE DESCRIPTION: SEQ ID NO:9:

| Gly | Asp | Lys | Asp | His | Met | Cys | Ser | Val | Lys | Ser | Arg | Leu | Trp | Lys | Leu |
|---|---|---|---|---|---|---|---|---|---|---|---|---|---|---|---|
| 1 | | | | 5 | | | | | 10 | | | | | 15 | |

| Leu | Ser | Pro | Ala | Arg | Leu | Ala | Arg | Arg | Ala | His | Arg | Ser | Lys | Trp | Leu |
|---|---|---|---|---|---|---|---|---|---|---|---|---|---|---|---|
| | | | 20 | | | | | 25 | | | | | 30 | | |

| Glu | Ser | Tyr | Leu | Leu | His | Leu | Glu | Glu | Met | Gly | Val | Ser | Glu | Glu | Met |
|---|---|---|---|---|---|---|---|---|---|---|---|---|---|---|---|
| | | 35 | | | | | 40 | | | | | 45 | | | |

| Gln | Ala | Arg | Ala | Leu | Val | Leu | Gln | Leu | Trp | Ala | Thr | Gln |
|---|---|---|---|---|---|---|---|---|---|---|---|---|
| | 50 | | | | | 55 | | | | | 60 | |

(2) INFORMATION FOR SEQ ID NO:10:

(i) SEQUENCE CHARACTERISTICS:
(A) LENGTH: 792 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Homo sapiens
(B) STRAIN: pHPGIS36

(ix) FEATURE:
(A) NAME/KEY: CDS
(B) LOCATION: 80..790

(ix) FEATURE:
(A) NAME/KEY: mat_peptide
(B) LOCATION: 80..790

(xi) SEQUENCE DESCRIPTION: SEQ ID NO:10:

```
CTACTACTAC TAGGCCACGC GTCGACTAGT ACGGGGGGGG GGGGGGGGGG GCAGCCCCGC      60

CAGCCCCGCC AGCCCCGCG ATG GCT TGG GCC GCG CTC CTC GGC CTC CTG GCC     112
                    Met Ala Trp Ala Ala Leu Leu Gly Leu Leu Ala
                     1               5                  10

GCA CTG TTG CTG CTG CTG CTA CTG AGC CGC CGC CGC ACG CGG CGA CCT     160
Ala Leu Leu Leu Leu Leu Leu Leu Ser Arg Arg Arg Thr Arg Arg Pro
            15                  20                  25

GGT GAG CCT CCC CTG GAC CTG GGC AGC ATC CCC TGG TTG GGG TAT GCC     208
Gly Glu Pro Pro Leu Asp Leu Gly Ser Ile Pro Trp Leu Gly Tyr Ala
        30                  35                  40

TTG GAC TTT GGA AAA GAT GCT GCC AGC TTC CTC ACG AGG ATG AAG GAG     256
Leu Asp Phe Gly Lys Asp Ala Ala Ser Phe Leu Thr Arg Met Lys Glu
    45                  50                  55

AAG CAC GGT GAC ATC TTT ACT ATA CTG GTT GGG GGC AGG TAT GTC ACC     304
Lys His Gly Asp Ile Phe Thr Ile Leu Val Gly Gly Arg Tyr Val Thr
60                  65                  70                  75

GTT CTC CTG GAC CCA CAC TCC TAC GAC GCG GTG GTG TGG GAG CCT CGC     352
Val Leu Leu Asp Pro His Ser Tyr Asp Ala Val Val Trp Glu Pro Arg
            80                  85                  90

ACC AGG CTC GAC TTC CAT GCC TAT GCC ATC TTC CTC ATG GAG AGG ATT     400
Thr Arg Leu Asp Phe His Ala Tyr Ala Ile Phe Leu Met Glu Arg Ile
        95                  100                 105

TTT GAT GTG CAG CTT CCA CAT TAC AGC CCC AGT GAT GAA AAG GCC AGG     448
Phe Asp Val Gln Leu Pro His Tyr Ser Pro Ser Asp Glu Lys Ala Arg
    110                 115                 120

ATG AAA CTG ACT CTT CTC CAC AGA GAG CTC CAG GCA CTC ACA GAA GCC     496
```

|  |  |  |  |  |  |  |  |  |  |  |  |  |  |  |  |
|---|---|---|---|---|---|---|---|---|---|---|---|---|---|---|---|
| Met | Lys 125 | Leu | Thr | Leu | Leu | His 130 | Arg | Glu | Leu | Gln | Ala 135 | Leu | Thr | Glu | Ala |
| ATG | TAT | ACC | AAC | CTC | CAT | GCA | GTG | CTG | TTG | GGC | GAT | GCT | ACA | GAA | GCA | 544 |
| Met 140 | Tyr | Thr | Asn | Leu | His 145 | Ala | Val | Leu | Leu | Gly 150 | Asp | Ala | Thr | Glu | Ala 155 |
| GGC | AGT | GGC | TGG | CAC | GAG | ATG | GGT | CTC | CTC | GAC | TTC | TCC | TAC | AGC | TTC | 592 |
| Gly | Ser | Gly | Trp | His 160 | Glu | Met | Gly | Leu | Leu 165 | Asp | Phe | Ser | Tyr | Ser 170 | Phe |
| CTG | CTC | AGA | GCC | GGC | TAC | CTG | ACT | CTT | TAC | GGA | ATT | GAG | GCG | CTG | CCA | 640 |
| Leu | Leu | Arg | Ala 175 | Gly | Tyr | Leu | Thr | Leu 180 | Tyr | Gly | Ile | Glu | Ala 185 | Leu | Pro |
| CGC | ACC | CAT | GAA | AGC | CAG | GCC | CAG | GAC | CGC | GTC | CAC | TCA | GCT | GAT | GTC | 688 |
| Arg | Thr | His 190 | Glu | Ser | Gln | Ala 195 | Gln | Asp | Arg | Val | His 200 | Ser | Ala | Asp | Val |
| TTC | CAC | ACC | TTT | CGC | CAG | CTC | GAC | CGG | CTG | CTC | CCC | AAA | CTG | GCC | CGT | 736 |
| Phe | His 205 | Thr | Phe | Arg | Gln | Leu 210 | Asp | Arg | Leu | Leu | Pro 215 | Lys | Leu | Ala | Arg |
| GGC | TCC | CTG | TCA | GTG | GGG | GAC | AAG | GAC | CAC | ATG | TGC | AGT | GTC | AAA | AGT | 784 |
| Gly 220 | Ser | Leu | Ser | Val | Gly 225 | Asp | Lys | Asp | His | Met 230 | Cys | Ser | Val | Lys | Ser 235 |
| CGC | CTG | TG |  |  |  |  |  |  |  |  |  |  |  |  |  | 792 |
| Arg | Leu |  |  |  |  |  |  |  |  |  |  |  |  |  |  |

( 2 ) INFORMATION FOR SEQ ID NO:11:

( i ) SEQUENCE CHARACTERISTICS:
        ( A ) LENGTH: 237 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

|  |  |  |  |  |  |  |  |  |  |  |  |  |  |  |
|---|---|---|---|---|---|---|---|---|---|---|---|---|---|---|
| Met 1 | Ala | Trp | Ala | Ala 5 | Leu | Leu | Gly | Leu | Leu 10 | Ala | Ala | Leu | Leu | Leu 15 | Leu |
| Leu | Leu | Leu | Ser 20 | Arg | Arg | Arg | Thr | Arg 25 | Arg | Pro | Gly | Glu | Pro 30 | Pro | Leu |
| Asp | Leu | Gly 35 | Ser | Ile | Pro | Trp | Leu 40 | Gly | Tyr | Ala | Leu | Asp 45 | Phe | Gly | Lys |
| Asp | Ala 50 | Ala | Ser | Phe | Leu | Thr 55 | Arg | Met | Lys | Glu | Lys 60 | His | Gly | Asp | Ile |
| Phe 65 | Thr | Ile | Leu | Val | Gly 70 | Gly | Arg | Tyr | Val | Thr 75 | Val | Leu | Leu | Asp | Pro 80 |
| His | Ser | Tyr | Asp | Ala 85 | Val | Val | Trp | Glu | Pro 90 | Arg | Thr | Arg | Leu | Asp 95 | Phe |
| His | Ala | Tyr | Ala 100 | Ile | Phe | Leu | Met | Glu 105 | Arg | Ile | Phe | Asp | Val 110 | Gln | Leu |
| Pro | His | Tyr 115 | Ser | Pro | Ser | Asp | Glu 120 | Lys | Ala | Arg | Met | Lys 125 | Leu | Thr | Leu |
| Leu | His 130 | Arg | Glu | Leu | Gln | Ala 135 | Leu | Thr | Glu | Ala | Met 140 | Tyr | Thr | Asn | Leu |
| His 145 | Ala | Val | Leu | Leu | Gly 150 | Asp | Ala | Thr | Glu | Ala 155 | Gly | Ser | Gly | Trp | His 160 |
| Glu | Met | Gly | Leu | Leu 165 | Asp | Phe | Ser | Tyr | Ser 170 | Phe | Leu | Leu | Arg | Ala 175 | Gly |
| Tyr | Leu | Thr | Leu 180 | Tyr | Gly | Ile | Glu | Ala 185 | Leu | Pro | Arg | Thr | His 190 | Glu | Ser |
| Gln | Ala | Gln 195 | Asp | Arg | Val | His | Ser 200 | Ala | Asp | Val | Phe | His 205 | Thr | Phe | Arg |

```
Gln  Leu  Asp  Arg  Leu  Leu  Pro  Lys  Leu  Ala  Arg  Gly  Ser  Leu  Ser  Val
     210                      215                      220

Gly  Asp  Lys  Asp  His  Met  Cys  Ser  Val  Lys  Ser  Arg  Leu
225                      230                      235
```

( 2 ) INFORMATION FOR SEQ ID NO:12:

( i ) SEQUENCE CHARACTERISTICS:
        ( A ) LENGTH: 1296 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens
        ( B ) STRAIN: pHPGIS135

( i x ) FEATURE:
        ( A ) NAME/KEY: CDS
        ( B ) LOCATION: 3..827

( i x ) FEATURE:
        ( A ) NAME/KEY: mat_peptide
        ( B ) LOCATION: 3..827

( x i ) SEQUENCE DESCRIPTION: SEQ ID NO:12:

```
GG  GAC  AAG  GAC  CAC  ATG  TGC  AGT  GTC  AAA  AGT  CGC  CTG  TGG  AAG  CTG        47
    Asp  Lys  Asp  His  Met  Cys  Ser  Val  Lys  Ser  Arg  Leu  Trp  Lys  Leu
    1                   5                        10                       15

CTA  TCC  CCA  GCC  AGG  CTG  GCC  AGG  CGG  GCC  CAC  CGG  AGC  AAA  TGG  CTG        95
Leu  Ser  Pro  Ala  Arg  Leu  Ala  Arg  Arg  Ala  His  Arg  Ser  Lys  Trp  Leu
               20                        25                       30

GAG  AGT  TAC  CTG  CTG  CAC  CTG  GAG  GAG  ATG  GGT  GTG  TCA  GAG  GAG  ATG       143
Glu  Ser  Tyr  Leu  Leu  His  Leu  Glu  Glu  Met  Gly  Val  Ser  Glu  Glu  Met
               35                        40                       45

CAG  GCA  CGG  GCC  CTG  GTG  CTG  CAG  CTG  TGG  GCC  ACA  CAG  GGG  AAT  ATG       191
Gln  Ala  Arg  Ala  Leu  Val  Leu  Gln  Leu  Trp  Ala  Thr  Gln  Gly  Asn  Met
               50                        55                       60

GGT  CCC  GCT  GCC  TTC  TGG  CTC  CTG  CTC  TTC  CTT  CTC  AAG  AAT  CCT  GAA       239
Gly  Pro  Ala  Ala  Phe  Trp  Leu  Leu  Leu  Phe  Leu  Leu  Lys  Asn  Pro  Glu
     65                        70                       75

GCC  CTG  GCT  GCT  GTC  CGC  GGA  GAG  CTC  GAG  AGT  ATC  CTT  TGG  CAA  GCG       287
Ala  Leu  Ala  Ala  Val  Arg  Gly  Glu  Leu  Glu  Ser  Ile  Leu  Trp  Gln  Ala
80                       85                        90                       95

GAG  CAG  CCT  GTC  TCG  CAG  ACG  ACC  ACT  CTC  CCA  CAG  AAG  GTT  CTA  GAC       335
Glu  Gln  Pro  Val  Ser  Gln  Thr  Thr  Thr  Leu  Pro  Gln  Lys  Val  Leu  Asp
               100                       105                      110

AGC  ACA  CCT  GTG  CTT  GAT  AGC  GTG  CTG  AGT  GAG  AGC  CTC  AGG  CTT  ACA       383
Ser  Thr  Pro  Val  Leu  Asp  Ser  Val  Leu  Ser  Glu  Ser  Leu  Arg  Leu  Thr
               115                       120                      125

GCT  GCC  CCC  TTC  ATC  ACC  CGC  GAG  GTT  GTG  GTG  GAC  CTG  GCC  ATG  CCC       431
Ala  Ala  Pro  Phe  Ile  Thr  Arg  Glu  Val  Val  Val  Asp  Leu  Ala  Met  Pro
          130                       135                      140

ATG  GCA  GAC  GGG  AGA  GAA  TTC  AAC  CTG  CGA  CGT  GGT  GAC  CGC  CTC  CTC       479
Met  Ala  Asp  Gly  Arg  Glu  Phe  Asn  Leu  Arg  Arg  Gly  Asp  Arg  Leu  Leu
     145                      150                      155

CTC  TTC  CCC  TTC  CTG  AGC  CCC  CAG  AGA  GAC  CCA  GAA  ATC  TAC  ACA  GAC       527
Leu  Phe  Pro  Phe  Leu  Ser  Pro  Gln  Arg  Asp  Pro  Glu  Ile  Tyr  Thr  Asp
160                      165                       170                      175

CCA  GAG  GTA  TTT  AAA  TAC  AAC  CGA  TTC  CTG  AAC  CCT  GAC  GGA  TCA  GAG       575
Pro  Glu  Val  Phe  Lys  Tyr  Asn  Arg  Phe  Leu  Asn  Pro  Asp  Gly  Ser  Glu
               180                       185                      190
```

```
AAG  AAA  GAC  TTT  TAC  AAG  GAT  GGG  AAA  CGG  CTG  AAG  AAT  TAC  AAC  ATG       623
Lys  Lys  Asp  Phe  Tyr  Lys  Asp  Gly  Lys  Arg  Leu  Lys  Asn  Tyr  Asn  Met
               195                      200                      205

CCC  TGG  GGG  GCG  GGG  CAC  AAT  CAC  TGC  CTG  GGG  AGG  AGT  TAT  GCG  GTC       671
Pro  Trp  Gly  Ala  Gly  His  Asn  His  Cys  Leu  Gly  Arg  Ser  Tyr  Ala  Val
          210                      215                      220

AAC  AGC  ATC  AAA  CAA  TTT  GTG  TTC  CTT  GTG  CTG  GTG  CAC  TTG  GAC  TTG       719
Asn  Ser  Ile  Lys  Gln  Phe  Val  Phe  Leu  Val  Leu  Val  His  Leu  Asp  Leu
     225                      230                      235

GAG  CTG  ATC  AAC  GCA  GAT  GTG  GAG  ATC  CCT  GAG  TTT  GAC  CTC  AGC  AGG       767
Glu  Leu  Ile  Asn  Ala  Asp  Val  Glu  Ile  Pro  Glu  Phe  Asp  Leu  Ser  Arg
240                      245                      250                      255

TAC  GGC  TTC  GGT  CTG  ATG  CAG  CCG  GAA  CAC  GAC  GTG  CCC  GTC  CGC  TAC       815
Tyr  Gly  Phe  Gly  Leu  Met  Gln  Pro  Glu  His  Asp  Val  Pro  Val  Arg  Tyr
                    260                      265                      270

CGC  ATC  CGC  CCA  TGACACAGGG  AGCAGATGGA  TCCACGTGCT  CGCCTCTGCC                    867
Arg  Ile  Arg  Pro
               275

CAGCCTGCCC  CAGCCTGCCC  CAGCCTCCCA  GCTTTCTGTG  TGCACAGTTG  GCCCGGGTGC                927

AGGTGCTAGC  ATTACCACTT  CCCTGCTTTT  CTCCCAGAAG  GCTGGGTCCA  GGGGAGGGAA                987

AAGCTAAGAG  GGTGAACAAA  GAAAAGACAT  TGAAAGCTCT  ATGGATTATC  CACTGCAAAG               1047

TTTTCTTTCC  AAAATCAGGC  TTTGTCTGCT  CCCAATTCAC  CTCGTTACTC  TCACCTCGTG               1107

ATATCCACAA  ATGCTATTCA  GATAAGGCAG  AACTAGGAGT  CTTCACTGCT  CTGCCCCCAA               1167

CTCCCGGAGG  TGTCACCTTC  CTAGTTCTTA  TGAGCTAGCA  TGGCCCGGGC  CTTATCCAGT               1227

CAAAGCGGAT  GCTGGCCACA  GAAAGGCCAC  TCAGGATGTC  CTTTGTGTCC  ATCGATGTCG               1287

ACTCGAGTC                                                                           1296
```

( 2 ) INFORMATION FOR SEQ ID NO:13:

( i ) SEQUENCE CHARACTERISTICS:
        ( A ) LENGTH: 275 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Asp  Lys  Asp  His  Met  Cys  Ser  Val  Lys  Ser  Arg  Leu  Trp  Lys  Leu  Leu
 1              5                        10                       15

Ser  Pro  Ala  Arg  Leu  Ala  Arg  Arg  Ala  His  Arg  Ser  Lys  Trp  Leu  Glu
               20                        25                       30

Ser  Tyr  Leu  Leu  His  Leu  Glu  Glu  Met  Gly  Val  Ser  Glu  Met  Gln
               35                        40                       45

Ala  Arg  Ala  Leu  Val  Leu  Gln  Leu  Trp  Ala  Thr  Gln  Gly  Asn  Met  Gly
     50                        55                       60

Pro  Ala  Ala  Phe  Trp  Leu  Leu  Phe  Leu  Leu  Lys  Asn  Pro  Glu  Ala
65                        70                       75                       80

Leu  Ala  Ala  Val  Arg  Gly  Glu  Leu  Glu  Ser  Ile  Leu  Trp  Gln  Ala  Glu
                    85                        90                       95

Gln  Pro  Val  Ser  Gln  Thr  Thr  Thr  Leu  Pro  Gln  Lys  Val  Leu  Asp  Ser
                    100                       105                      110

Thr  Pro  Val  Leu  Asp  Ser  Val  Leu  Ser  Glu  Ser  Leu  Arg  Leu  Thr  Ala
               115                       120                      125

Ala  Pro  Phe  Ile  Thr  Arg  Glu  Val  Val  Val  Asp  Leu  Ala  Met  Pro  Met
     130                       135                      140

Ala  Asp  Gly  Arg  Glu  Phe  Asn  Leu  Arg  Arg  Gly  Asp  Arg  Leu  Leu  Leu
```

```
145                      150                     155                       160
Phe Pro Phe Leu Ser Pro Gln Arg Asp Pro Glu Ile Tyr Thr Asp Pro
                165                 170                 175

Glu Val Phe Lys Tyr Asn Arg Phe Leu Asn Pro Asp Gly Ser Glu Lys
            180                 185                 190

Lys Asp Phe Tyr Lys Asp Gly Lys Arg Leu Lys Asn Tyr Asn Met Pro
            195                 200                 205

Trp Gly Ala Gly His Asn His Cys Leu Gly Arg Ser Tyr Ala Val Asn
        210                 215                 220

Ser Ile Lys Gln Phe Val Phe Leu Val Leu Val His Leu Asp Leu Glu
225                 230                 235                     240

Leu Ile Asn Ala Asp Val Glu Ile Pro Glu Phe Asp Leu Ser Arg Tyr
                245                 250                 255

Gly Phe Gly Leu Met Gln Pro Glu His Asp Val Pro Val Arg Tyr Arg
                260                 265                 270

Ile Arg Pro
        275
```

( 2 ) INFORMATION FOR SEQ ID NO:14:

( i ) SEQUENCE CHARACTERISTICS:
        ( A ) LENGTH: 1977 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: CDS
        ( B ) LOCATION: 28..1527

( i x ) FEATURE:
        ( A ) NAME/KEY: mat_peptide
        ( B ) LOCATION: 28..1527

( x i ) SEQUENCE DESCRIPTION: SEQ ID NO:14:

```
AGCCCCGCCA GCCCCGCCAG CCCCGCG ATG GCT TGG GCC GCG CTC CTC GGC            51
                              Met Ala Trp Ala Ala Leu Leu Gly
                               1                   5

CTC CTG GCC GCA CTG TTG CTG CTG CTA CTG AGC CGC CGC CGC ACG              99
Leu Leu Ala Ala Leu Leu Leu Leu Leu Leu Ser Arg Arg Arg Thr
         10                  15                  20

CGG CGA CCT GGT GAG CCT CCC CTG GAC CTG GGC AGC ATC CCC TGG TTG         147
Arg Arg Pro Gly Glu Pro Pro Leu Asp Leu Gly Ser Ile Pro Trp Leu
 25                  30                  35                  40

GGG TAT GCC TTG GAC TTT GGA AAA GAT GCT GCC AGC TTC CTC ACG AGG         195
Gly Tyr Ala Leu Asp Phe Gly Lys Asp Ala Ala Ser Phe Leu Thr Arg
                 45                  50                  55

ATG AAG GAG AAG CAC GGT GAC ATC TTT ACT ATA CTG GTT GGG GGC AGG         243
Met Lys Glu Lys His Gly Asp Ile Phe Thr Ile Leu Val Gly Gly Arg
                     60                  65                  70

TAT GTC ACC GTT CTC CTG GAC CCA CAC TCC TAC GAC GCG GTG GTG TGG         291
Tyr Val Thr Val Leu Leu Asp Pro His Ser Tyr Asp Ala Val Val Trp
             75                  80                  85

GAG CCT CGC ACC AGG CTC GAC TTC CAT GCC TAT GCC ATC TTC CTC ATG         339
Glu Pro Arg Thr Arg Leu Asp Phe His Ala Tyr Ala Ile Phe Leu Met
         90                  95                 100

GAG AGG ATT TTT GAT GTG CAG CTT CCA CAT TAC AGC CCC AGT GAT GAA         387
Glu Arg Ile Phe Asp Val Gln Leu Pro His Tyr Ser Pro Ser Asp Glu
```

```
                   105                           110                           115                           120
AAG  GCC  AGG  ATG  AAA  CTG  ACT  CTT  CTC  CAC  AGA  GAG  CTC  CAG  GCA  CTC                435
Lys  Ala  Arg  Met  Lys  Leu  Thr  Leu  Leu  His  Arg  Glu  Leu  Gln  Ala  Leu
                    125                           130                           135

ACA  GAA  GCC  ATG  TAT  ACC  AAC  CTC  CAT  GCA  GTG  CTG  TTG  GGC  GAT  GCT                483
Thr  Glu  Ala  Met  Tyr  Thr  Asn  Leu  His  Ala  Val  Leu  Leu  Gly  Asp  Ala
                    140                           145                           150

ACA  GAA  GCA  GGC  AGT  GGC  TGG  CAC  GAG  ATG  GGT  CTC  CTC  GAC  TTC  TCC                531
Thr  Glu  Ala  Gly  Ser  Gly  Trp  His  Glu  Met  Gly  Leu  Leu  Asp  Phe  Ser
               155                           160                           165

TAC  AGC  TTC  CTG  CTC  AGA  GCC  GGC  TAC  CTG  ACT  CTT  TAC  GGA  ATT  GAG                579
Tyr  Ser  Phe  Leu  Leu  Arg  Ala  Gly  Tyr  Leu  Thr  Leu  Tyr  Gly  Ile  Glu
          170                           175                           180

GCG  CTG  CCA  CGC  ACC  CAT  GAA  AGC  CAG  GCC  CAG  GAC  CGC  GTC  CAC  TCA                627
Ala  Leu  Pro  Arg  Thr  His  Glu  Ser  Gln  Ala  Gln  Asp  Arg  Val  His  Ser
185                           190                           195                           200

GCT  GAT  GTC  TTC  CAC  ACC  TTT  CGC  CAG  CTC  GAC  CGG  CTG  CTC  CCC  AAA                675
Ala  Asp  Val  Phe  His  Thr  Phe  Arg  Gln  Leu  Asp  Arg  Leu  Leu  Pro  Lys
                              205                           210                           215

CTG  GCC  CGT  GGC  TCC  CTG  TCA  GTG  GGG  GAC  AAG  GAC  CAC  ATG  TGC  AGT                723
Leu  Ala  Arg  Gly  Ser  Leu  Ser  Val  Gly  Asp  Lys  Asp  His  Met  Cys  Ser
                    220                           225                           230

GTC  AAA  AGT  CGC  CTG  TGG  AAG  CTG  CTA  TCC  CCA  GCC  AGG  CTG  GCC  AGG                771
Val  Lys  Ser  Arg  Leu  Trp  Lys  Leu  Leu  Ser  Pro  Ala  Arg  Leu  Ala  Arg
          235                           240                           245

CGG  GCC  CAC  CGG  AGC  AAA  TGG  CTG  GAG  AGT  TAC  CTG  CTG  CAC  CTG  GAG                819
Arg  Ala  His  Arg  Ser  Lys  Trp  Leu  Glu  Ser  Tyr  Leu  Leu  His  Leu  Glu
          250                           255                           260

GAG  ATG  GGT  GTG  TCA  GAG  GAG  ATG  CAG  GCA  CGG  GCC  CTG  GTG  CTG  CAG                867
Glu  Met  Gly  Val  Ser  Glu  Glu  Met  Gln  Ala  Arg  Ala  Leu  Val  Leu  Gln
265                           270                           275                           280

CTG  TGG  GCC  ACA  CAG  GGG  AAT  ATG  GGT  CCC  GCT  GCC  TTC  TGG  CTC  CTG                915
Leu  Trp  Ala  Thr  Gln  Gly  Asn  Met  Gly  Pro  Ala  Ala  Phe  Trp  Leu  Leu
                    285                           290                           295

CTC  TTC  CTT  CTC  AAG  AAT  CCT  GAA  GCC  CTG  GCT  GCT  GTC  CGC  GGA  GAG                963
Leu  Phe  Leu  Leu  Lys  Asn  Pro  Glu  Ala  Leu  Ala  Ala  Val  Arg  Gly  Glu
               300                           305                           310

CTC  GAG  AGT  ATC  CTT  TGG  CAA  GCG  GAG  CAG  CCT  GTC  TCG  CAG  ACG  ACC               1011
Leu  Glu  Ser  Ile  Leu  Trp  Gln  Ala  Glu  Gln  Pro  Val  Ser  Gln  Thr  Thr
          315                           320                           325

ACT  CTC  CCA  CAG  AAG  GTT  CTA  GAC  AGC  ACA  CCT  GTG  CTT  GAT  AGC  GTG               1059
Thr  Leu  Pro  Gln  Lys  Val  Leu  Asp  Ser  Thr  Pro  Val  Leu  Asp  Ser  Val
     330                           335                           340

CTG  AGT  GAG  AGC  CTC  AGG  CTT  ACA  GCT  GCC  CCC  TTC  ATC  ACC  CGC  GAG               1107
Leu  Ser  Glu  Ser  Leu  Arg  Leu  Thr  Ala  Ala  Pro  Phe  Ile  Thr  Arg  Glu
345                           350                           355                           360

GTT  GTG  GTG  GAC  CTG  GCC  ATG  CCC  ATG  GCA  GAC  GGG  AGA  GAA  TTC  AAC               1155
Val  Val  Val  Asp  Leu  Ala  Met  Pro  Met  Ala  Asp  Gly  Arg  Glu  Phe  Asn
                    365                           370                           375

CTG  CGA  CGT  GGT  GAC  CGC  CTC  CTC  CTC  TTC  CCC  TTC  CTG  AGC  CCC  CAG               1203
Leu  Arg  Arg  Gly  Asp  Arg  Leu  Leu  Leu  Phe  Pro  Phe  Leu  Ser  Pro  Gln
                    380                           385                           390

AGA  GAC  CCA  GAA  ATC  TAC  ACA  GAC  CCA  GAG  GTA  TTT  AAA  TAC  AAC  CGA               1251
Arg  Asp  Pro  Glu  Ile  Tyr  Thr  Asp  Pro  Glu  Val  Phe  Lys  Tyr  Asn  Arg
               395                           400                           405

TTC  CTG  AAC  CCT  GAC  GGA  TCA  GAG  AAG  AAA  GAC  TTT  TAC  AAG  GAT  GGG               1299
Phe  Leu  Asn  Pro  Asp  Gly  Ser  Glu  Lys  Lys  Asp  Phe  Tyr  Lys  Asp  Gly
          410                           415                           420

AAA  CGG  CTG  AAG  AAT  TAC  AAC  ATG  CCC  TGG  GGG  GCG  GGG  CAC  AAT  CAC               1347
Lys  Arg  Leu  Lys  Asn  Tyr  Asn  Met  Pro  Trp  Gly  Ala  Gly  His  Asn  His
```

|       |       |       |       | 425   |       |       |       | 430   |       |       |       | 435   |       |       |       | 440   |      |
|-------|-------|-------|-------|-------|-------|-------|-------|-------|-------|-------|-------|-------|-------|-------|-------|-------|------|
| TGC   | CTG   | GGG   | AGG   | AGT   | TAT   | GCG   | GTC   | AAC   | AGC   | ATC   | AAA   | CAA   | TTT   | GTG   | TTC   |       | 1395 |
| Cys   | Leu   | Gly   | Arg   | Ser   | Tyr   | Ala   | Val   | Asn   | Ser   | Ile   | Lys   | Gln   | Phe   | Val   | Phe   |       |      |
|       |       |       |       | 445   |       |       |       |       | 450   |       |       |       |       | 455   |       |       |      |
| CTT   | GTG   | CTG   | GTG   | CAC   | TTG   | GAC   | TTG   | GAG   | CTG   | ATC   | AAC   | GCA   | GAT   | GTG   | GAG   |       | 1443 |
| Leu   | Val   | Leu   | Val   | His   | Leu   | Asp   | Leu   | Glu   | Leu   | Ile   | Asn   | Ala   | Asp   | Val   | Glu   |       |      |
|       |       |       | 460   |       |       |       |       | 465   |       |       |       |       | 470   |       |       |       |      |
| ATC   | CCT   | GAG   | TTT   | GAC   | CTC   | AGC   | AGG   | TAC   | GGC   | TTC   | GGT   | CTG   | ATG   | CAG   | CCG   |       | 1491 |
| Ile   | Pro   | Glu   | Phe   | Asp   | Leu   | Ser   | Arg   | Tyr   | Gly   | Phe   | Gly   | Leu   | Met   | Gln   | Pro   |       |      |
|       |       | 475   |       |       |       |       | 480   |       |       |       |       | 485   |       |       |       |       |      |
| GAA   | CAC   | GAC   | GTG   | CCC   | GTC   | CGC   | TAC   | CGC   | ATC   | CGC   | CCA   | TGACACAGGG |  |  |  |       | 1537 |
| Glu   | His   | Asp   | Val   | Pro   | Val   | Arg   | Tyr   | Arg   | Ile   | Arg   | Pro   |       |       |       |       |       |      |
|       | 490   |       |       |       | 495   |       |       |       |       | 500   |       |       |       |       |       |       |      |

| AGCAGATGGA | TCCACGTGCT | CGCCTCTGCC | CAGCCTGCCC | CAGCCTGCCC | CAGCCTCCCA | 1597 |
| GCTTTCTGTG | TGCACAGTTG | GCCCGGGTGC | AGGTGCTAGC | ATTACCACTT | CCCTGCTTTT | 1657 |
| CTCCCAGAAG | GCTGGGTCCA | GGGGAGGGAA | AAGCTAAGAG | GGTGAACAAA | GAAAAGACAT | 1717 |
| TGAAAGCTCT | ATGGATTATC | CACTGCAAAG | TTTTCTTTCC | AAAATCAGGC | TTTGTCTGCT | 1777 |
| CCCAATTCAC | CTCGTTACTC | TCACCTCGTG | ATATCCACAA | ATGCTATTCA | GATAAGGCAG | 1837 |
| AACTAGGAGT | CTTCACTGCT | CTGCCCCCAA | CTCCCGGAGG | TGTCACCTTC | CTAGTTCTTA | 1897 |
| TGAGCTAGCA | TGGCCCGGGC | CTTATCCAGT | CAAAGCGGAT | GCTGGCCACA | GAAAGGCCAC | 1957 |
| TCAGGATGTC | CTTTGTGTCC |            |            |            |            | 1977 |

(2) INFORMATION FOR SEQ ID NO:15:

(i) SEQUENCE CHARACTERISTICS:
        (A) LENGTH: 500 amino acids
        (B) TYPE: amino acid
        (D) TOPOLOGY: linear (ii) MOLECULE TYPE: protein (xi) SEQUENCE DESCRIPTION: SEQ ID NO:15:

| Met | Ala | Trp | Ala | Ala | Leu | Leu | Gly | Leu | Leu | Ala | Ala | Leu | Leu | Leu | Leu |
|---|---|---|---|---|---|---|---|---|---|---|---|---|---|---|---|
| 1 |  |  |  | 5 |  |  |  |  | 10 |  |  |  |  | 15 |  |
| Leu | Leu | Leu | Ser | Arg | Arg | Arg | Thr | Arg | Arg | Pro | Gly | Glu | Pro | Pro | Leu |
|  |  |  | 20 |  |  |  |  | 25 |  |  |  |  | 30 |  |  |
| Asp | Leu | Gly | Ser | Ile | Pro | Trp | Leu | Gly | Tyr | Ala | Leu | Asp | Phe | Gly | Lys |
|  |  |  | 35 |  |  |  |  | 40 |  |  |  |  | 45 |  |  |
| Asp | Ala | Ala | Ser | Phe | Leu | Thr | Arg | Met | Lys | Glu | Lys | His | Gly | Asp | Ile |
|  |  | 50 |  |  |  |  | 55 |  |  |  |  | 60 |  |  |  |
| Phe | Thr | Ile | Leu | Val | Gly | Gly | Arg | Tyr | Val | Thr | Val | Leu | Leu | Asp | Pro |
| 65 |  |  |  |  | 70 |  |  |  |  | 75 |  |  |  |  | 80 |
| His | Ser | Tyr | Asp | Ala | Val | Val | Trp | Glu | Pro | Arg | Thr | Arg | Leu | Asp | Phe |
|  |  |  |  | 85 |  |  |  |  | 90 |  |  |  |  | 95 |  |
| His | Ala | Tyr | Ala | Ile | Phe | Leu | Met | Glu | Arg | Ile | Phe | Asp | Val | Gln | Leu |
|  |  |  | 100 |  |  |  |  | 105 |  |  |  |  | 110 |  |  |
| Pro | His | Tyr | Ser | Pro | Ser | Asp | Glu | Lys | Ala | Arg | Met | Lys | Leu | Thr | Leu |
|  |  | 115 |  |  |  |  | 120 |  |  |  |  | 125 |  |  |  |
| Leu | His | Arg | Glu | Leu | Gln | Ala | Leu | Thr | Glu | Ala | Met | Tyr | Thr | Asn | Leu |
|  | 130 |  |  |  |  | 135 |  |  |  |  | 140 |  |  |  |  |
| His | Ala | Val | Leu | Leu | Gly | Asp | Ala | Thr | Glu | Ala | Gly | Ser | Gly | Trp | His |
| 145 |  |  |  |  | 150 |  |  |  |  | 155 |  |  |  |  | 160 |
| Glu | Met | Gly | Leu | Leu | Asp | Phe | Ser | Tyr | Ser | Phe | Leu | Leu | Arg | Ala | Gly |
|  |  |  |  | 165 |  |  |  |  | 170 |  |  |  |  | 175 |  |
| Tyr | Leu | Thr | Leu | Tyr | Gly | Ile | Glu | Ala | Leu | Pro | Arg | Thr | His | Glu | Ser |

|     |     |     |     | 180 |     |     |     |     | 185 |     |     |     |     | 190 |     |
|-----|-----|-----|-----|-----|-----|-----|-----|-----|-----|-----|-----|-----|-----|-----|-----|

Gln Ala Gln Asp Arg Val His Ser Ala Asp Val Phe His Thr Phe Arg
        195             200             205

Gln Leu Asp Arg Leu Leu Pro Lys Leu Ala Arg Gly Ser Leu Ser Val
    210             215             220

Gly Asp Lys Asp His Met Cys Ser Val Lys Ser Arg Leu Trp Lys Leu
225             230             235             240

Leu Ser Pro Ala Arg Leu Ala Arg Arg Ala His Arg Ser Lys Trp Leu
            245             250             255

Glu Ser Tyr Leu Leu His Leu Glu Glu Met Gly Val Ser Glu Glu Met
        260             265             270

Gln Ala Arg Ala Leu Val Leu Gln Leu Trp Ala Thr Gln Gly Asn Met
        275             280             285

Gly Pro Ala Ala Phe Trp Leu Leu Leu Phe Leu Leu Lys Asn Pro Glu
290             295             300

Ala Leu Ala Ala Val Arg Gly Glu Leu Glu Ser Ile Leu Trp Gln Ala
305             310             315             320

Glu Gln Pro Val Ser Gln Thr Thr Thr Leu Pro Gln Lys Val Leu Asp
            325             330             335

Ser Thr Pro Val Leu Asp Ser Val Leu Ser Glu Ser Leu Arg Leu Thr
            340             345             350

Ala Ala Pro Phe Ile Thr Arg Glu Val Val Val Asp Leu Ala Met Pro
            355             360             365

Met Ala Asp Gly Arg Glu Phe Asn Leu Arg Arg Gly Asp Arg Leu Leu
        370             375             380

Leu Phe Pro Phe Leu Ser Pro Gln Arg Asp Pro Glu Ile Tyr Thr Asp
385             390             395             400

Pro Glu Val Phe Lys Tyr Asn Arg Phe Leu Asn Pro Asp Gly Ser Glu
            405             410             415

Lys Lys Asp Phe Tyr Lys Asp Gly Lys Arg Leu Lys Asn Tyr Asn Met
            420             425             430

Pro Trp Gly Ala Gly His Asn His Cys Leu Gly Arg Ser Tyr Ala Val
        435             440             445

Asn Ser Ile Lys Gln Phe Val Phe Leu Val Leu Val His Leu Asp Leu
450             455             460

Glu Leu Ile Asn Ala Asp Val Glu Ile Pro Glu Phe Asp Leu Ser Arg
465             470             475             480

Tyr Gly Phe Gly Leu Met Gln Pro Glu His Asp Val Pro Val Arg Tyr
            485             490             495

Arg Ile Arg Pro
        500

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PRIMER/SYNTHETIC DNA"

( x i ) SEQUENCE DESCRIPTION: SEQ ID NO:16:

GACAAGGACC ACATGTGCAG TGTC        24

( 2 ) INFORMATION FOR SEQ ID NO:17:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "PRIMER/SYNTHETIC DNA"

( x i ) SEQUENCE DESCRIPTION: SEQ ID NO:17:

CTGTGTGGCC  CACAGCTGCA  GCAC                              2 4